United States Patent
Shin et al.

(10) Patent No.: US 8,119,814 B2
(45) Date of Patent: Feb. 21, 2012

(54) AROMATIC HETROCYCLIC COMPOUND, ORGANIC LIGHT-EMITTING DIODE INCLUDING ORGANIC LAYER COMPRISING THE AROMATIC HETROCYCLIC COMPOUND, AND METHOD OF MANUFACTURING THE ORGANIC LIGHT-EMITTING DIODE

(75) Inventors: Dong-woo Shin, Yongin-si (KR); Myeong-suk Kim, Yongin-si (KR); Tae-woo Lee, Yongin-si (KR); Yu-jin Kim, Yongin-si (KR); Eun-sil Han, Yongin-si (KR); Woon-jung Paek, Yongin-si (KR); Yu-ri Choi, Yongin-si (KR); Byoung-ki Choi, Yongin-si (KR); Tae-yong Noh, Yongin-si (KR); O-hyun Kwon, Yongin-si (KR); Haa-jin Yang, Yongin-si (KR); Young-mok Son, Yongin-si (KR)

(73) Assignees: Samsung Electronics Co., Ltd., Yeongtong-gu, Suwon-si, Gyeonggi-do (KR); Samsung Mobile Display Co., Ltd., Giheung-Gu, Yongin, Gyunggi-Do (KR)

( * ) Notice: Subject to any disclaimer, the term of this patent is extended or adjusted under 35 U.S.C. 154(b) by 857 days.

(21) Appl. No.: 12/149,371

(22) Filed: Apr. 30, 2008

(65) Prior Publication Data

US 2009/0149649 A1    Jun. 11, 2009

(30) Foreign Application Priority Data

Dec. 7, 2007   (KR) .......................... 10-2007-0126910

(51) Int. Cl.
*H01L 51/00*   (2006.01)
*H01L 51/50*   (2006.01)
(52) U.S. Cl. ...................................... 548/310.7; 257/40
(58) Field of Classification Search ............... 548/310.7
See application file for complete search history.

(56) References Cited

U.S. PATENT DOCUMENTS 4,356,429 A     10/1982   Tang
7,851,071 B2 *  12/2010   Yamamoto et al. ........... 428/690

FOREIGN PATENT DOCUMENTS

JP        11-003782        1/1999
WO   WO-2004/080975 A1 *  9/2004

* cited by examiner

*Primary Examiner* — Laura L. Stockton
(74) *Attorney, Agent, or Firm* — Robert E. Bushnell, Esq.

(57) ABSTRACT

The present invention provides an aromatic heterocyclic compound represented by Formula 1 below, an organic light-emitting diode including an organic layer comprising the aromatic heterocyclic compound, and a method of manufacturing the organic light-emitting diode:

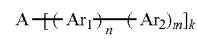

wherein A, $Ar_1$, $Ar_2$, n, m, and k are as described in the detailed description of the present invention.

19 Claims, 5 Drawing Sheets

AROMATIC HETROCYCLIC COMPOUND, ORGANIC LIGHT-EMITTING DIODE INCLUDING ORGANIC LAYER COMPRISING THE AROMATIC HETROCYCLIC COMPOUND, AND METHOD OF MANUFACTURING THE ORGANIC LIGHT-EMITTING DIODE

CLAIM OF PRIORITY

This application claims the benefit of Korean Patent Application No. 10-2007-0126910, filed on Dec. 7, 2007, in the Korean Intellectual Property Office, the disclosure of which is incorporated herein in its entirety by reference.

BACKGROUND OF THE INVENTION

1. Field of the Invention

The present invention relates to an aromatic heterocyclic compound, an organic light-emitting diode including the same, and a method of manufacturing the organic light-emitting diode, and more particularly, to an aromatic heterocyclic compound with excellent light-emitting characteristics, providing a low driving voltage, high efficiency, high brightness, high color purity and long life span when used in an organic light-emitting diode, and an organic light-emitting diode including an organic layer comprising the aromatic heterocyclic compound, and a method of manufacturing the organic light-emitting diode.

2. Description of the Related Art

Organic light-emitting diodes (OLED) are subject to intensive research due to their high brightness, low driving voltage, quick response time, and polychromatic characteristics.

Conventionally, OLEDs have a stacked structure of anode/organic emission layer/cathode, and may also have diverse structures such as anode/hole injection layer/hole transport layer/emission layer/electron transport layer/electron injection layer/cathode, and anode/hole injection layer/hole transport layer/emission layer/hole blocking layer/electron transport layer/electron injection layer/cathode.

Materials used for OLEDs may be classified into vacuum deposited materials and solution deposited materials, according to the method of manufacturing an organic layer of the OLEDs. The vacuum deposited materials should conventionally have a vapor pressure of $10^{-6}$ torr or higher, at 500° C. or less. In this regard, low-molecular weight materials with a mean molecular weight of 1200 or less are mainly used as vacuum deposited materials. The solution deposited material should have a high solubility to a solvent for forming a solution. The main types of solution deposited material include aromatic or heterocyclic compounds.

When OLEDs are manufactured using a vacuum deposition method, the usage of a vacuum system increases the manufacturing costs, and when a shadow mask is used in order to produce natural display pixels, it is difficult to produce high-resolution pixels. In contrast, solution deposition methods such as inkjet printing, screen-printing, and spin coating provide a convenient method of manufacturing an organic layer and at a low cost, and provide a higher resolution when compared to using a shadow mask.

However, conventional materials that are used for solution deposition are inferior in terms of thermostability and color purity, compared to the materials used for vacuum deposition. Moreover, even if the solution deposited materials have superior characteristics than the materials used for vacuum deposition, crystals of the deposited material are gradually formed after an organic layer is manufactured. The crystals have a size in the visible light wavelength range, scattering visible light and exhibiting white residues, and forming pin holes, and thus there is a strong likelihood of degradation of the OLED.

In Japanese Patent Laid-open Publication No. 1999-003782, an anthracene substituted with 2 naphthyl groups is disclosed as a compound that can be used for an emission layer. However, the compound has poor solubility for the solvent, and the characteristics of the OLED using the compound are not satisfactory.

Thus, development of a compound which can be used in an organic layer of an OLED so that the organic layer can have excellent thermostability and light-emitting characteristic regardless of the method of manufacturing the organic layer, is in demand.

SUMMARY OF THE INVENTION

According to an aspect of the present invention, there is provided an aromatic heterocyclic compound represented by Formula 1 below:

(Formula 1)

wherein A is substituted or unsubstituted benzo[k]fluoranthene or substituted or unsubstituted chrysene;
$Ar_1$ is substituted or unsubstituted $C_5$-$C_{12}$ arylene group,
n is an integer in the range of 0 to 6,
$Ar_2$ is a terminal group of Formula 2 below;
m is an integer in the range of 1 to 6; and
k is an integer in the range of 1 to 4:

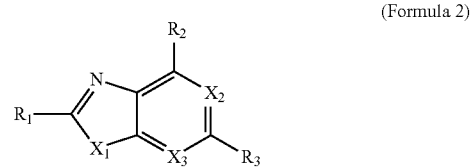

(Formula 2)

wherein $X_1$ is one of $N(R_4)$, S, Se, and Te;
$X_2$ and $X_3$ are each independently $C(R_5)$ or N; and
at least one of $R_1$ to $R_5$ is a linkage site to A or Ar1 of Formula 1 above, and the remaining groups of $R_1$ to $R_5$ that are not linkage sites to A or Ar1 are each independently hydrogen, halogen, cyano group, nitro group, hydroxyl group, substituted or unsubstituted $C_1$-$C_{20}$ alkyl group, substituted or unsubstituted $C_2$-$C_{20}$ alkenyl group, substituted or unsubstituted $C_2$-$C_{20}$ alkynyl group, substituted or unsubstituted $C_5$-$C_{20}$ cycloalkyl group, substituted or unsubstituted $C_5$-$C_{20}$ cycloalkenyl group, substituted or unsubstituted $C_5$-$C_{20}$ aryl group, substituted or unsubstituted $C_2$-$C_{30}$ heteroaryl group, or a group represented by —$N(Z_1)(Z_2)$, wherein $Z_1$ and $Z_2$ are independently hydrogen, substituted or unsubstituted $C_1$-$C_{20}$ alkyl group, or substituted or unsubstituted $C_5$-$C_{20}$ aryl group.

According to another aspect of the present invention, there is provided an organic light-emitting diode including a first electrode, a second electrode, and an organic layer between the first electrode and the second electrode, including an aromatic heterocyclic compound represented by Formula 1 as previously described.

According to yet another aspect of the present invention, there is provided a method of preparing an organic light-emitting diode including: forming a first electrode on a substrate; forming an organic layer including an aromatic heterocyclic compound represented by Formula 1 as previously described on the first electrode; and forming a second electrode on the organic layer.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings in which like reference symbols indicate the same or similar components, wherein.

DETAILED DESCRIPTION OF THE INVENTION

Figure 1A:
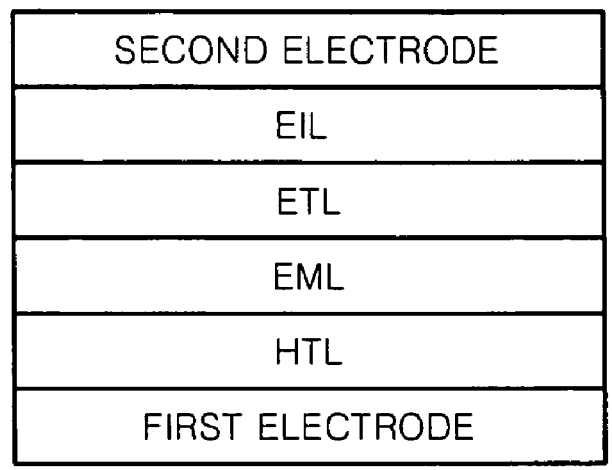
FIGS. 1A to 1C are cross-sectional views of organic light-emitting diodes according to embodiments of the present invention.

Hereinafter, the present invention will be described more fully with reference to the accompanying drawings, in which preferred embodiments of the invention are shown.

An aromatic heterocyclic compound according to the present invention is represented by Formula 1 below:

(Formula 1)

wherein A is substituted or unsubstituted benzo[k]fluoranthene or substituted or unsubstituted chrysene.

A acts to improve thermostability and optical efficiency. Such an aromatic heterocyclic compound including A can have excellent light-emitting characteristics, and can prevent deterioration of an organic light-emitting diode including an organic layer comprising the aromatic heterocyclic compound while operating, thereby achieving long life span.

To illustrate A in more detail, the aromatic heterocyclic compound of the present invention may also be represented by Formula 1a below:

(Formula 1a)

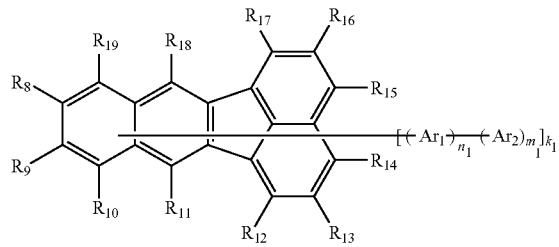

wherein $n_1$ is an integer in the range of 1 to 6, $m_1$ is an integer in the range of 1 to 6, and $k_1$ is an integer in the range of 1 to 4, and $Ar_1$ and $Ar_2$ are to be described later. Meanwhile, k represents the number of linkage sites to $Ar_1$ among $R_8$ to $R_{19}$. Meanwhile, the remaining groups of $R_8$ to $R_{19}$ that are not linkage sites to $Ar_1$ may each independently be one of hydrogen, halogen, cyano group, nitro group, hydroxyl group, substituted or unsubstituted $C_1$-$C_{20}$ alkyl group, substituted or unsubstituted $C_2$-$C_{20}$ alkenyl group, substituted or unsubstituted $C_2$-$C_{20}$ alkynyl group, substituted or unsubstituted $C_5$-$C_{20}$ cycloalkyl group, substituted or unsubstituted $C_5$-$C_{20}$ cycloalkenyl group, substituted or unsubstituted $C_5$-$C_{60}$ aryl group, substituted or unsubstituted $C_2$-$C_{30}$ heteroaryl group, substituted and a group represented by —$N(Z_1)(Z_2)$ wherein $Z_1$ and $Z_2$ are each independently one of hydrogen, substituted or unsubstituted $C_1$-$C_{20}$ alkyl group, and substituted or unsubstituted $C_5$-$C_{20}$ aryl group.

The remaining groups among $R_8$ to $R_{19}$ that are not linkage sites to $Ar_1$ increase solubility and amorphous characteristic of the aromatic heterocyclic compound represented by Formula 1a, thereby enhancing the film-forming characteristics of the aromatic heterocyclic compound.

Preferably, $k_1$ represents the number of groups among $R_8$ to $R_{19}$ in Formula 1a that are linkage sites to $Ar_1$, and the remaining groups among $R_8$ to $R_{19}$ that are not linkage sites to $Ar_1$ may independently be one of hydrogen, halogen, cyano group, nitro group, hydroxyl group, substituted or unsubstituted $C_1$-$C_{10}$ alkyl group, substituted or unsubstituted $C_5$-$C_{14}$ aryl group, and substituted or unsubstituted $C_2$-$C_{14}$ heteroaryl group.

More preferably, at least one of $R_{11}$, $R_{14}$, $R_{15}$ and $R_{18}$ of Formula 1a may be linkage sites to $Ar_1$.

The aromatic heterocyclic compound of the present invention may also be represented by Formula 1b below:

(Formula 1b)

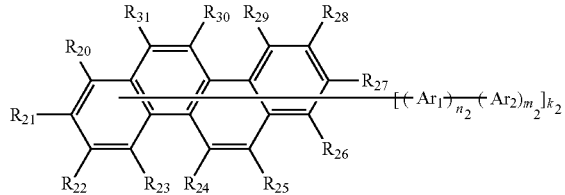

wherein $n_2$ is an integer in the range of 0 to 6, $m_2$ is an integer in the range of 1 to 6, $k_1$ is an integer in the range of 1 to 4, and $Ar_1$ and $Ar_2$ are to be described later on. Meanwhile, k represents the number of groups among $R_{20}$ to $R_{31}$ that are linkage sites to $Ar_1$ and $Ar_2$, and the remaining groups among $R_{20}$ to $R_{31}$ that are not linkage sites to $Ar_1$ and $Ar_2$ are each independently one of hydrogen, halogen, cyano group, nitro group, hydroxyl group, substituted or unsubstituted $C_1$-$C_{20}$alkyl group, substituted or unsubstituted $C_2$-$C_{20}$ alkenyl group, substituted or unsubstituted $C_2$-$C_{20}$ alkynyl group, substituted or unsubstituted $C_5$-$C_{20}$ cycloalkyl group, substituted or unsubstituted $C_5$-$C_{20}$ cycloalkenyl group, substituted or unsubstituted $C_5$-$C_{20}$ aryl group, substituted or unsubstituted $C_2$-$C_{30}$ heteroaryl group, substituted and a group represented by —$N(Z_1)(Z_2)$ wherein $Z_1$ and $Z_2$ are each independently one of hydrogen, substituted or unsubstituted $C_1$-$C_{20}$ alkyl group, and substituted or unsubstituted $C_5$-$C_{20}$ aryl group.

The remaining groups among $R_{20}$ to $R_{31}$ that are not linkage sites to $Ar_1$ and $Ar_2$ increase solubility and amorphous characteristics of the aromatic heterocyclic compound represented by Formula 1a, thereby enhancing the film-forming characteristics of the aromatic heterocyclic compound.

Preferably, $k_2$ represents the number of groups among $R_{20}$ to $R_{31}$ above that are linkage sites to one of $Ar_1$ and $Ar_2$, and the remaining groups among $R_{20}$ to $R_{31}$ that are not linkage sites to one of $Ar_1$ and $Ar_2$ may independently be one of hydrogen, halogen, cyano group, nitro group, hydroxyl group, substituted or unsubstituted $C_1$-$C_{10}$ alkyl group, substituted or unsubstituted $C_5$-$C_{14}$ aryl group, and substituted or unsubstituted $C_2$-$C_{14}$ heteroaryl group.

More particularly, A of Formula 1 may be one of the structures represented by Formula 3 below, but is not limited thereto:

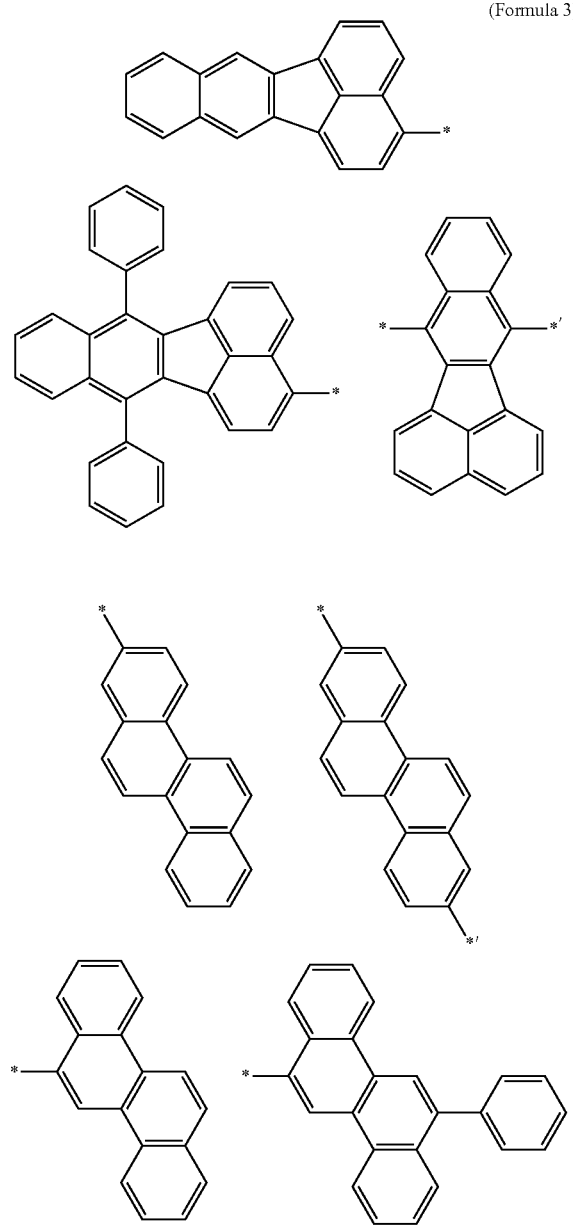

(Formula 3)

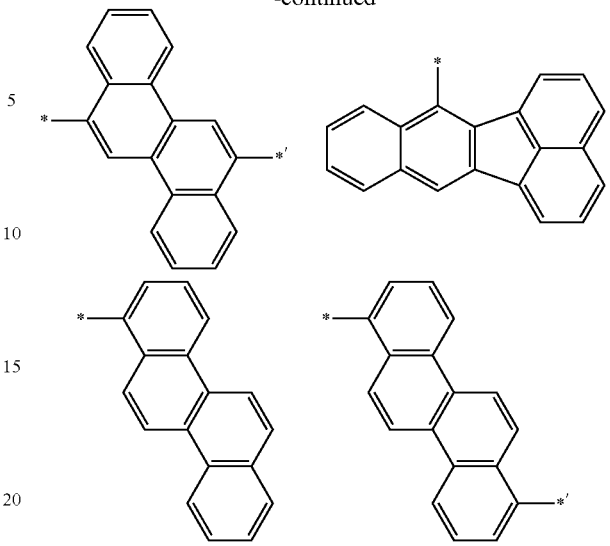

-continued wherein * and *' each independently represent linkage sites to $Ar_1$ or $Ar_2$.

$Ar_1$ of Formula 1 is a linking group existing between A and $Ar_2$, and may be a substituted or unsubstituted $C_5$-$C_{12}$ arylene group.

$Ar_1$ increases amorphic characteristics of a compound. When such $Ar_1$ is included, the aromatic heterocyclic compound has excellent light-emitting characteristics and can achieve long life span.

Preferably, $Ar_1$ may be one selected from the group consisting of phenylene, bromophenylene, chlorophenylene, fluorophenylene, cyanophenylene, $C_1$-$C_{10}$ alkylphenylene, $C_1$-$C_{10}$ alkoxyphenylene, naphthylphenylene, dinaphthylphenylene, naphthylene, bromonaphthylene, chloronaphthylene, fluoronaphthylene, cyanonaphthylene, $C_1$-$C_{10}$ alkylnaphthylene, $C_1$-$C_{10}$ alkoxynaphthylene, phenylnaphthylene, diphenyinaphthylene, and terphenylnaphthylene.

More specifically, —$(Ar_1)_n$— of Formula 1 may be one of the structures represented by Formula 4 below, but is not limited thereto:

(Formula 4)

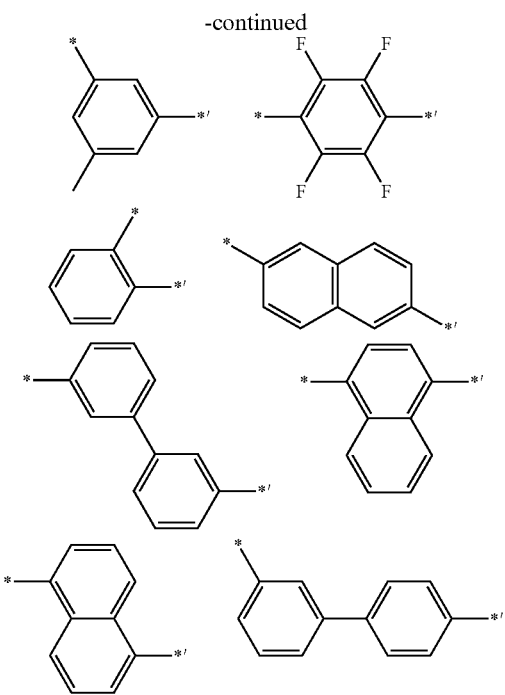

wherein * represents a linkage site to A and the *'s each represent linkage sites to $Ar_2$.

$Ar_2$ of Formula 1 is a terminal group including Formula 2 below:

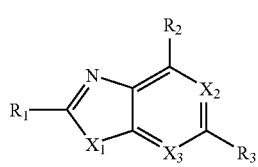

(Formula 2)

The terminal group having Formula 2 above has an electrophilic property, and thus has excellent electron transport characteristics. Therefore, the aromatic heterocyclic compound represented by Formula 1 according to the present invention may have excellent electron transport characteristics.

$X_1$ of Formula 2 may be one of $N(R_4)$, S, Se and Te, and $X_2$ and $X_3$ may each independently be one of $C(R_5)$ and N. Preferably, $X_2$ and $X_3$ may be the same.

One of $R_1$ to $R_5$ in Formula 2 may be a linkage site to A or $Ar_1$ of Formula 1 above, and the remaining groups of $R_1$ to $R_5$ that are not linkage sites to A or Ar1 may be each independently one selected from the group consisting of hydrogen, halogen, cyano group, nitro group, hydroxyl group, substituted or unsubstituted $C_1$-$C_{20}$ alkyl group, substituted or unsubstituted $C_2$-$C_{20}$ alkenyl group, substituted or unsubstituted $C_2$-$C_{30}$ alkynyl group, substituted or unsubstituted $C_5$-$C_{20}$ cycloalkyl group, substituted or unsubstituted $C_5$-$C_{20}$ cycloalkenyl group, substituted or unsubstituted $C_5$-$C_{20}$ aryl group, substituted or unsubstituted $C_2$-$C_{30}$ heteroaryl group, and a group represented by —$N(Z_1)(Z_2)$. Here, $Z_1$ and $Z_2$ may each independently be one of hydrogen, substituted or unsubstituted $C_1$-$C_{20}$ alkyl group, and substituted or unsubstituted $C_5$-$C_{20}$ aryl group.

The remaining groups among $R_1$ to $R_5$ that are not linkage sites to A or $Ar_1$ increase solubility and amorphous characteristics of the aromatic heterocyclic compound represented by Formula 1a, thereby enhancing the film-forming characteristics of the aromatic heterocyclic compound.

Preferably, one of $R_1$ to $R_5$ above is a linkage site to one of A and $Ar_1$, and the remaining groups among $R_1$ to $R_5$ that are not linkage sites to one of A and $Ar_1$ may independently be one of hydrogen, halogen, cyano group, nitro group, hydroxyl group, substituted or unsubstituted $C_1$-$C_{10}$ alkyl group, substituted or unsubstituted $C_5$-$C_{14}$ aryl group, substituted or unsubstituted $C_2$-$C_{14}$ heteroaryl group and a group represented by —$N(Z_1)(Z_2)$. Here, $Z_1$ and $Z_2$ are each independently one of hydrogen, substituted or unsubstituted $C_1$-$C_{20}$ alkyl group, and substituted or unsubstituted $C_5$-$C_{14}$ aryl group.

More preferably, one of $R_1$ and $R_2$ of Formula 2 may be a linkage site to one of A and $Ar_1$.

Meanwhile, $X_1$ of Formula 2 may be $N(R_4)$ or S, and $X_2$ and $X_3$ may independently be $C(R_5)$ or N.

More specifically, $Ar_2$ may be one of the structures represented by Formula 5 below, but is not limited thereto:

(Formula 5)

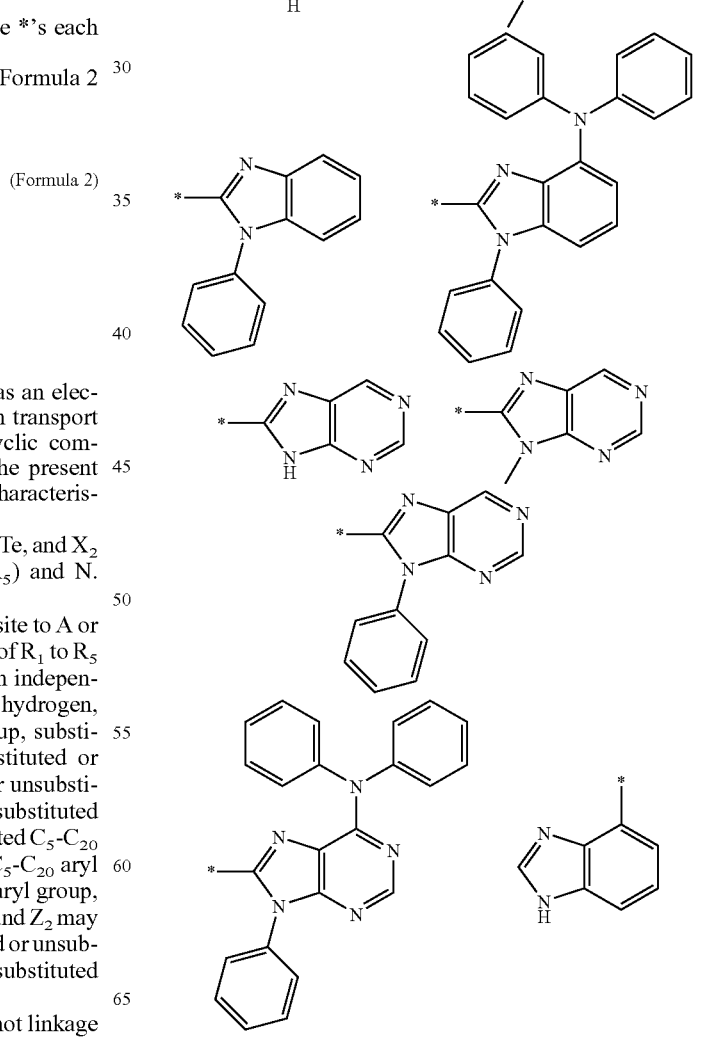

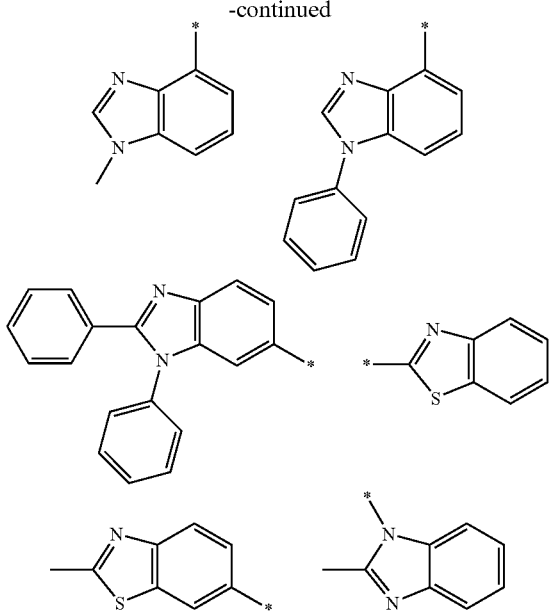

wherein * represents a linkage site to $Ar_1$.

In Formula 1, m may be an integer in the range of 1 to 6, and preferably an integer in the range of 1 to 3, and k may be an integer in the range of 1 to 4, and preferably 1 or 2, but m and k are not limited thereto.

Specific examples of unsubstituted $C_1$-$C_{20}$ alkyl group in the present specification include methyl, ethyl, propyl, isobutyl, sec-butyl, pentyl, iso-amyl, and hexyl, and at least one hydrogen within the alkyl group may be substituted with one of halogen atom, hydroxyl group, nitro group, cyano group, amino group, amidino group, hydrazine, hydrazone, carboxyl group and salts thereof, $C_1$-$C_{30}$ alkenyl group, $C_1$-$C_{30}$ alkynyl group, $C_6$-$C_{30}$ aryl group, $C_2$-$C_{20}$ heteroaryl group, and a group represented by —N($Q_1$)($Q_2$). Here, $Q_1$ and $Q_2$ may each independently be selected from the group consisting of hydrogen, $C_1$-$C_{30}$ alkyl group, $C_1$-$C_{30}$ haloalkyl group, $C_6$-$C_{30}$ aryl group, $C_6$-$C_{30}$ haloaryl group and $C_2$-$C_{30}$ heteroaryl group.

In the present specification, specific examples of unsubstituted $C_1$-$C_{20}$ alkoxy group include methoxy, ethoxy, phenyloxy, cyclohexyloxy, naphthyloxy, isopropyloxy, and diphenyloxy. At least one hydrogen atom within the alkoxy groups may be substituted with the same substituent groups as previously described for the alkyl groups above.

In the present specification, unsubstituted $C_2$-$C_{20}$ alkenyl group refers to a group containing a double carbon bond in the middle or the end of the alkyl group defined above. Examples of such groups include ethylene, propylene, butylene, and hexylene. At least one hydrogen atom of these alkenyl groups may be substituted with the same substituent groups as previously described for the alkyl groups.

In the present specification, unsubstituted $C_2$-$C_{20}$ alkynyl group refers to a group containing a triple carbon bond in the middle or the end of the alkyl group defined above. Examples of such groups include acetylene, propylene, phenylacetylene, naphthylacetylene, isopropyl acetylene, t-butyl acetylene, and diphenyl acetylene. At least one hydrogen atom within the alkynyl groups may be substituted with the same substituent groups as previously described for the alkyl groups above.

In the present specification, unsubstituted $C_5$-$C_{20}$ aryl group refers to a carbocyclic aromatic system of 5 to 20 carbon atoms including at least one aromatic ring, wherein the at least one ring may be fused together or may be connected by a single bond. At least one hydrogen atom within the aryl group may be substituted with the same substituent groups as previously described for the alkyl groups above.

In the present specification, examples of unsubstituted $C_5$-$C_{20}$ aryl group may include phenyl group, $C_1$-$C_{10}$ alkylphenyl group (such as ethylphenyl group), halophenyl group (such as o-, m-, and p-fluorophenyl group and dichlorophenyl group), cyanophenyl group, dicyanophenyl group, trifluoromethoxyphenyl group, biphenyl group, halobiphenyl group, cyanobiphenyl group $C_1$-$C_{10}$ biphenyl group, $C_1$-$C_{10}$ alkoxy biphenyl group, o-, m-, and p-tolyl group, o-, m-, and p-cumenyl group, mesityl group, phenoxyphenyl group, (α,α'-dimethylbenzene)phenyl group, (N,N'-dimethyl)aminophenyl group, (N,N'-diphenyl)aminophenyl group, pentalenyl group, indenyl group, naphthyl group, halonaphthyl group (such as fluoronaphthyl group), $C_1$-$C_{10}$ alkylnaphthyl group (such as methylnaphthyl group), $C_1$-$C_{10}$ alkoxynaphthyl group (such as methoxynaphthyl group), cyanonaphthyl group, anthracenyl group, azulenyl group, heptalenyl group, acenaphthyl group, phenalenyl group, fluorenyl group, anthraquinonyl group, methylanthryl group, phenanthryl group, triphenylene group, pyrenyl group, chrysenyl group, ethyl-chrysenyl group, picenyl group, perylenyl group, hexacenyl group, rubicenyl group, coroneryl group, trinaphthylenyl group, heptaphenyl group, heptacenyl group, pyranthrenyl group, and oparenyl group. Clearly, these may be substituted with the same substituent groups as previously described for the alkyl groups.

In the present specification, unsubstituted $C_5$-$C_{20}$ arylene group is a divalent linking group having a similar structure as the aryl group. Examples of such groups include phenylene group and naphthylene group, but are not limited thereto. At least one hydrogen atom among the arylene group may be substituted with the same substituent groups as previously described for the alkyl groups.

In the present specification, unsubstituted $C_2$-$C_{30}$ heteroaryl group refers to a system formed of at least one aromatic ring, including at least one heteroatom selected from the group consisting of N, O, P, and S, and the remaining ring atoms are C, and at least one aromatic ring may be fused together or may be connected by a single bond. At least one hydrogen atom of the heteroaryl groups may be substituted with the same substituent groups as previously described for the alkyl groups.

In the present specification, examples of unsubstituted $C_2$-$C_{30}$ heteroaryl groups include parazolyl group, imidazole group, oxazolyl group, thiazolyl group, triazolyl group, tetrazolyl group, oxadiazolyl group, pyridinyl group, pyridazinyl group, pyrimidinyl group, triazinyl group, carbazolyl group, indolyl group, quinolinyl group, and isoquinolinyl group. Clearly, these may be substituted with the same substituent groups as previously described for the alkyl groups.

In the present specification, unsubstituted $C_5$-$C_{20}$ cycloalkyl group refers to an alkyl group with a ring system, and unsubstituted $C_5$-$C_{20}$ cycloalkenyl group refers to an alkenyl group with a ring system. At least one hydrogen atom within the cycloalkyl group and the cycloalkenyl group may be substituted with the same substituent groups as previously described for the alkyl groups.

According to an embodiment of the present invention, the aromatic heterocyclic compound represented by Formula 1 of the present invention may be represented by one of Formulae 1 to 35 below, but is not limited thereto:

(Formula 1)
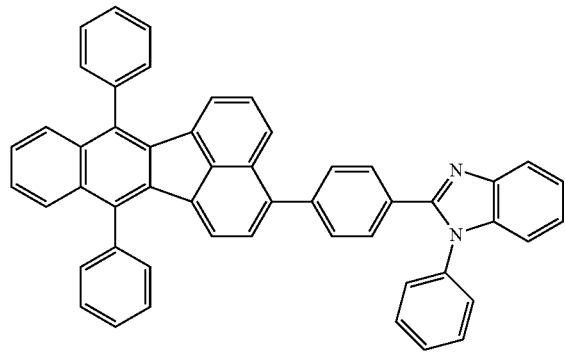
(Formula 2)
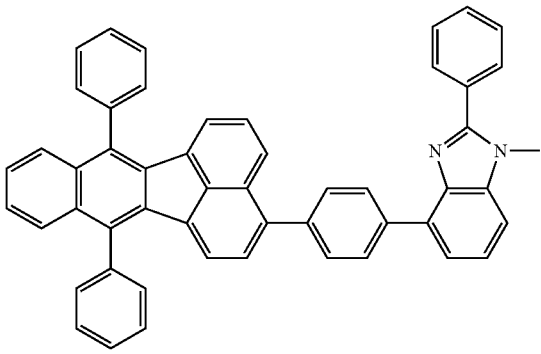
(Formula 3)
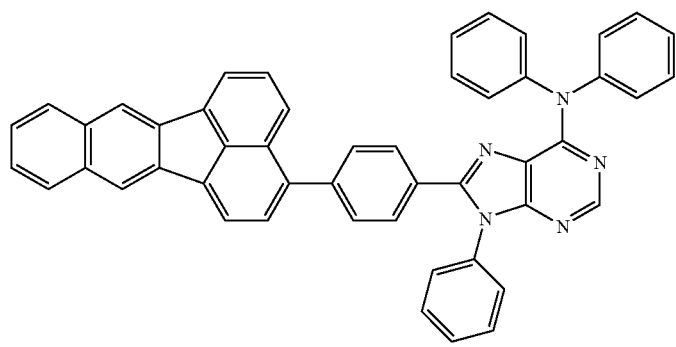
(Formula 4)
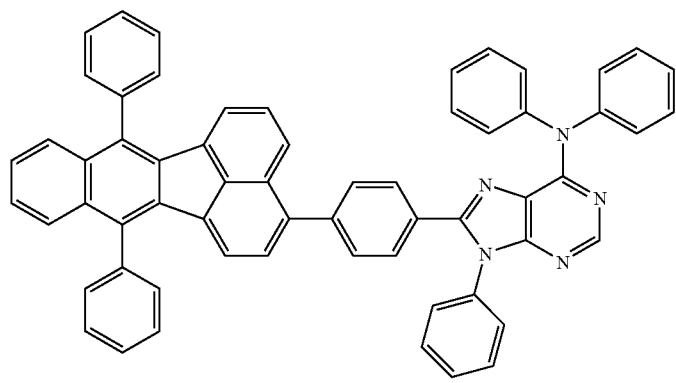
(Formula 5)
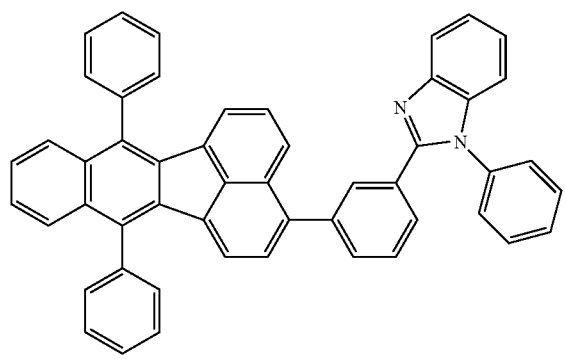
(Formula 6)
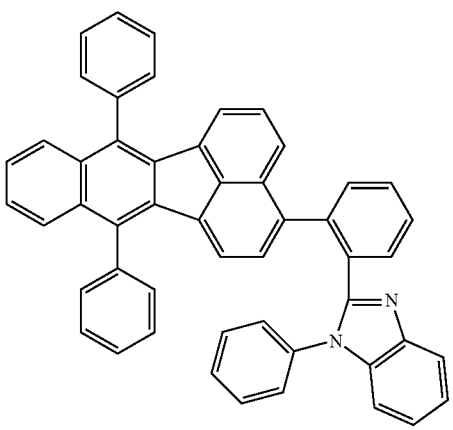

-continued
(Formula 7)
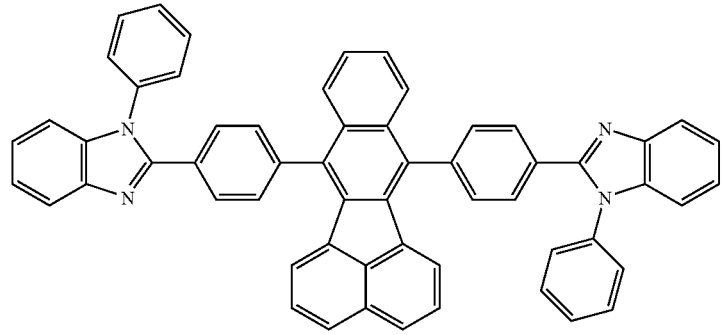
(Formula 8)
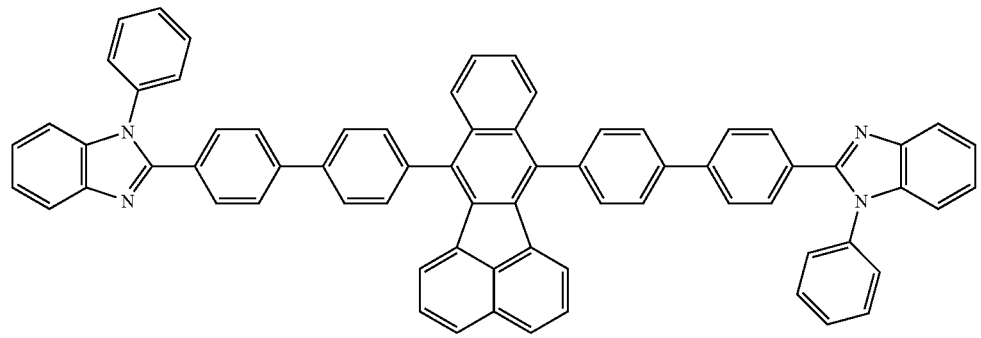
(Formula 9)
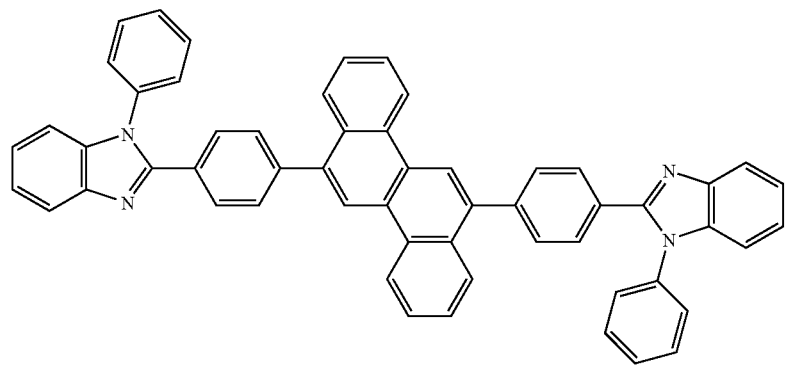
(Formula 10)
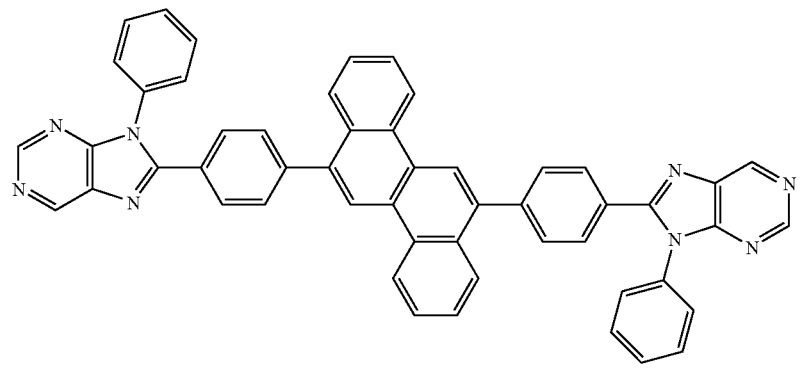

-continued
(Formula 11)
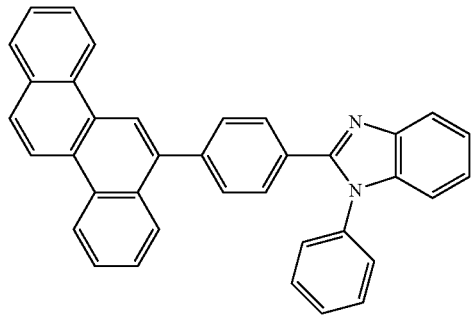
(Formula 12)
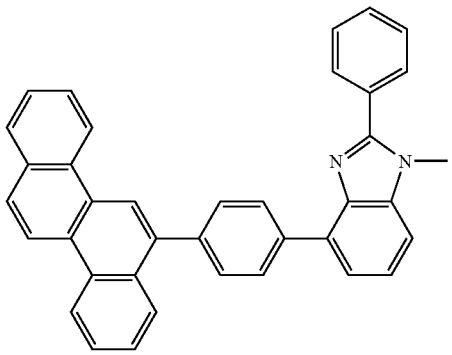
(Formula 13)
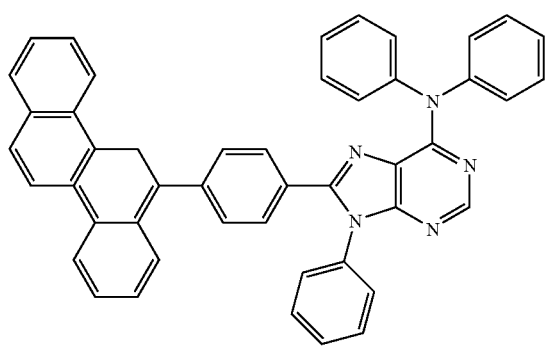
(Formula 14)
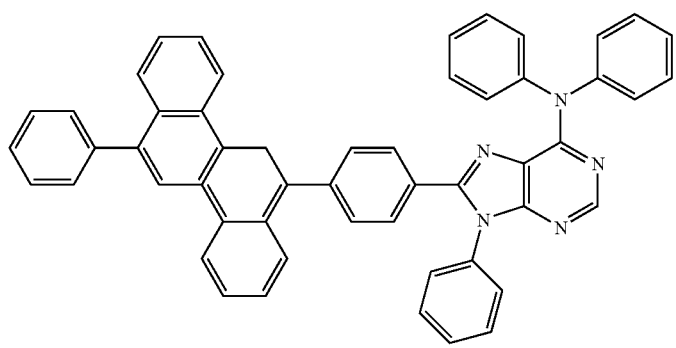
(Formula 15)
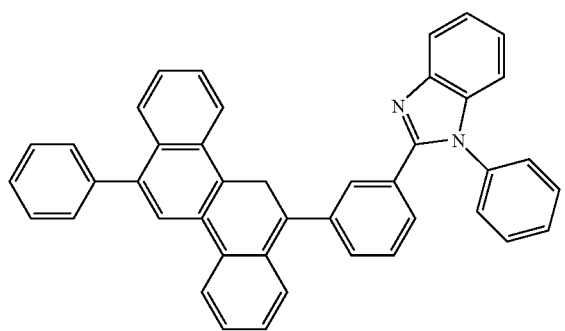

(Formula 16)
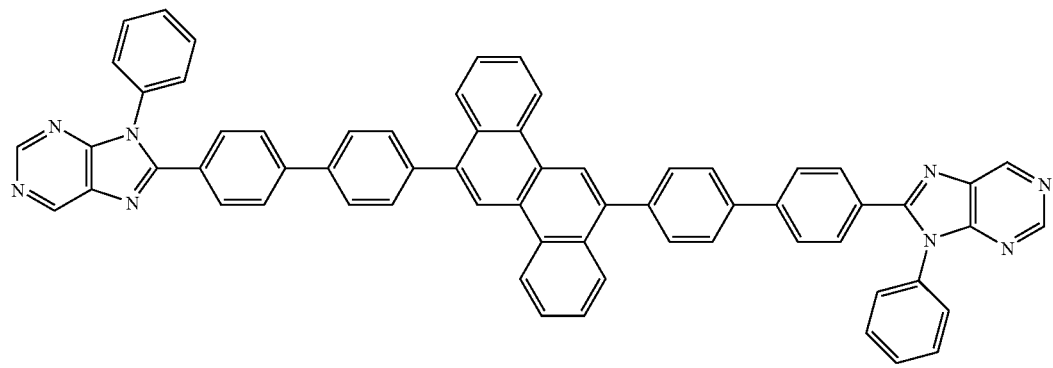
(Formula 17)
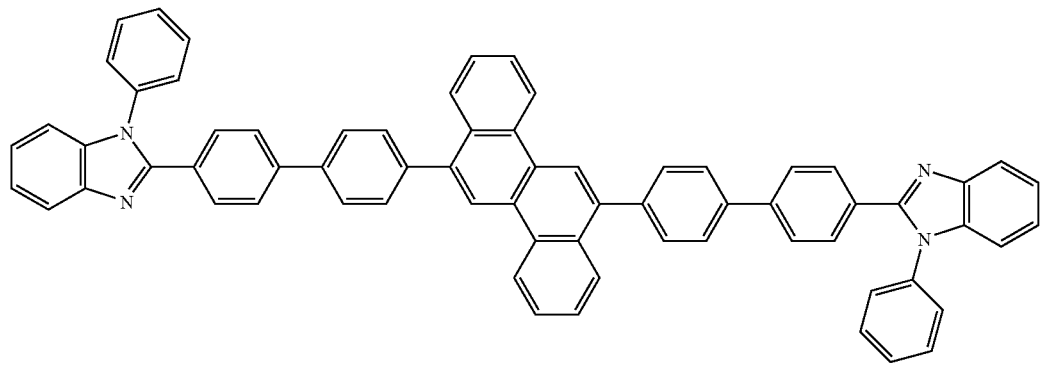
(Formula 18) (Formula 19)
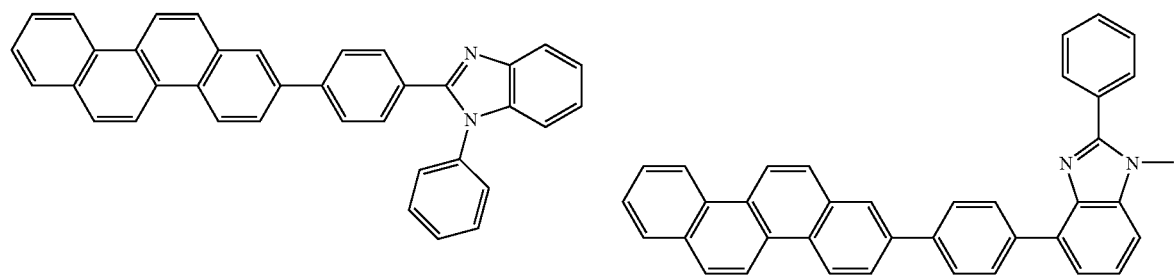
(Formula 20)
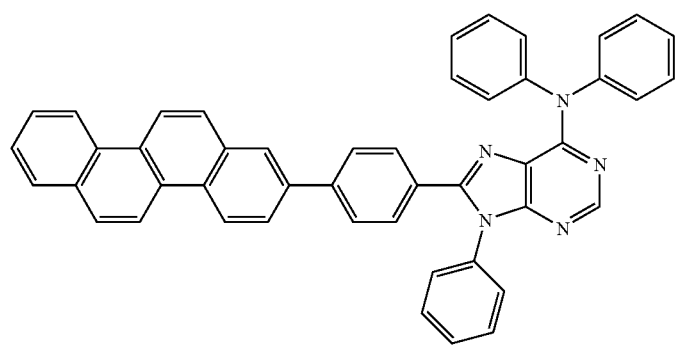

-continued
(Formula 21)
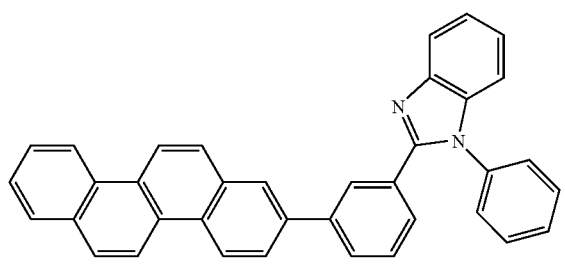
(Formula 22)
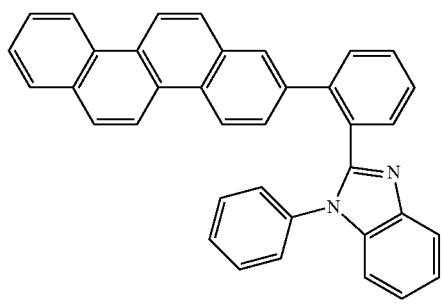
(Formula 23)
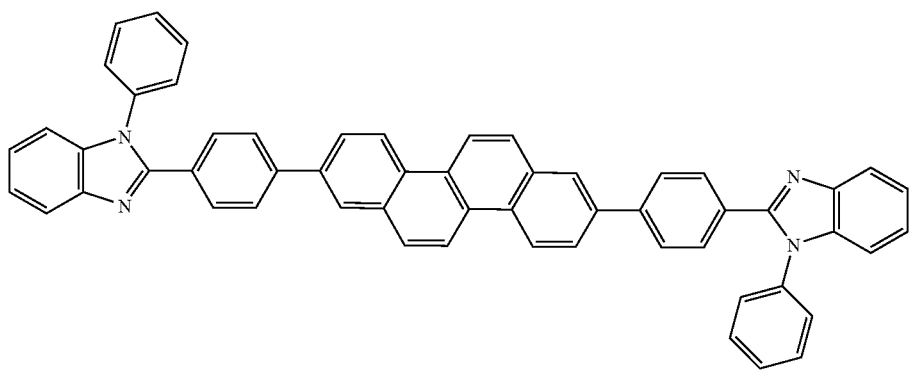
(Formula 24)
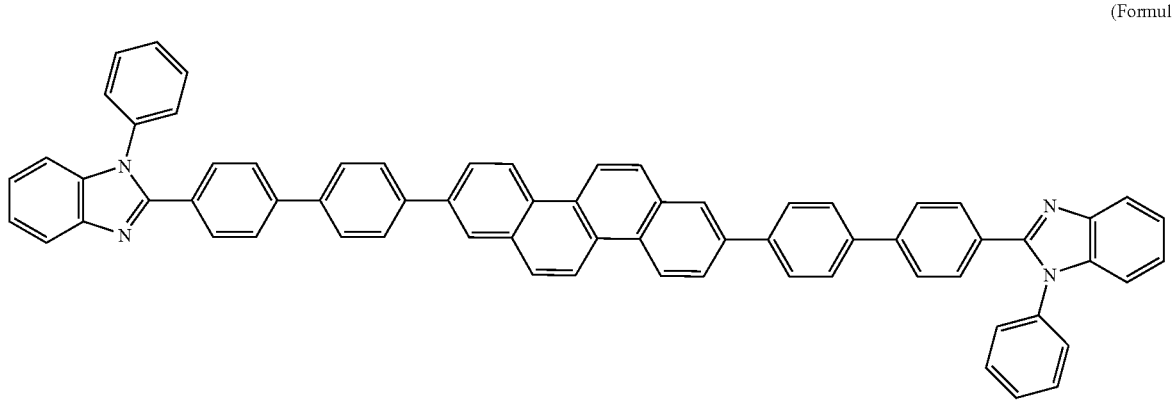
(Formula 25)
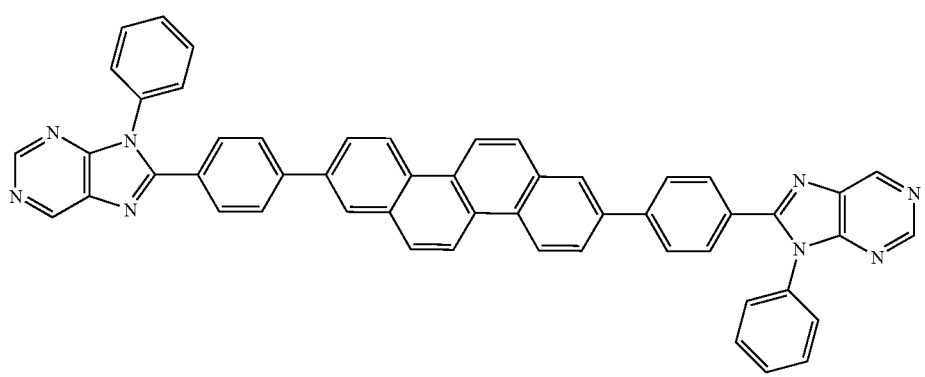

-continued
(Formula 26)
(Formula 27)
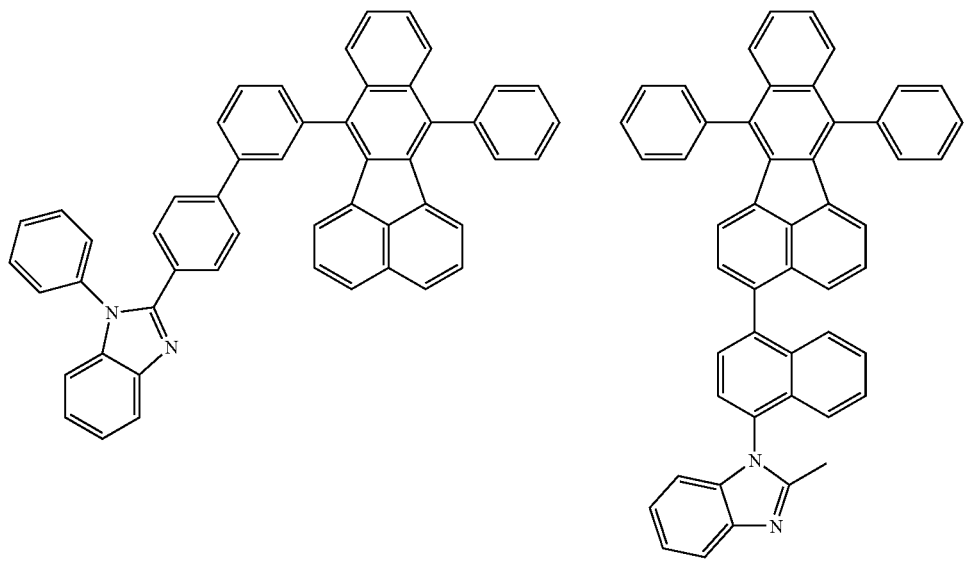
(Formula 28)
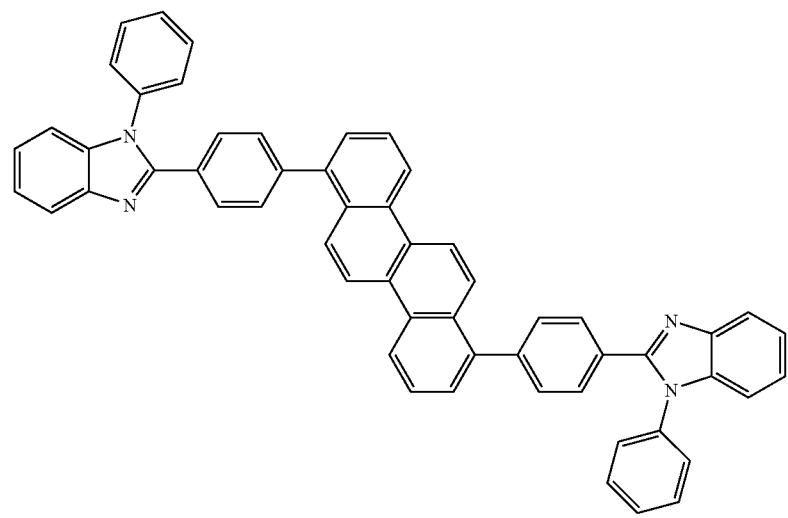
(Formula 29)
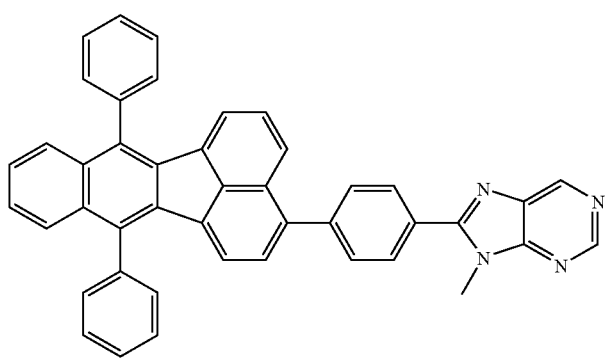

-continued
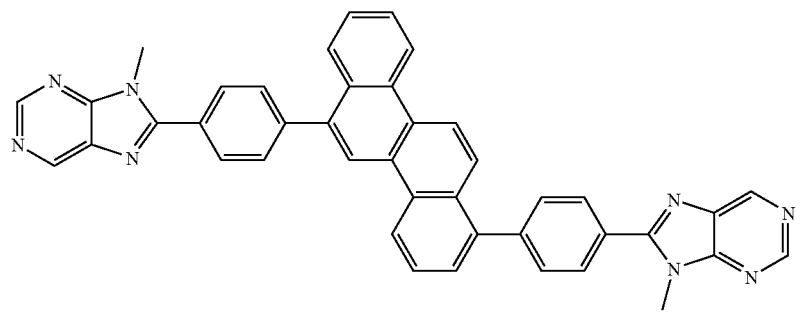
(Formula 30)
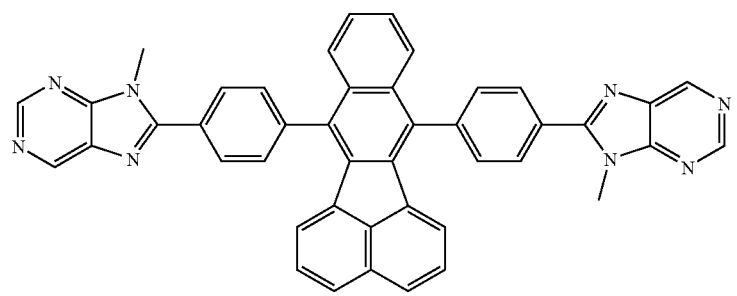
(Formula 31)
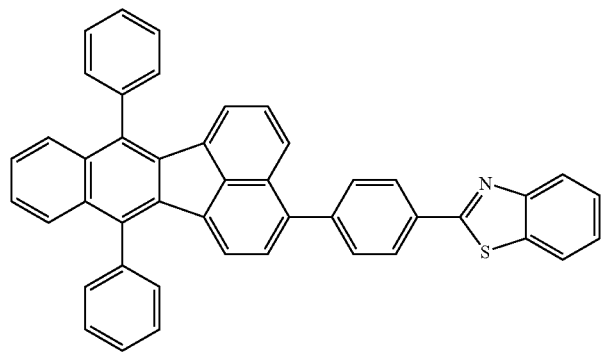
(Formula 32)
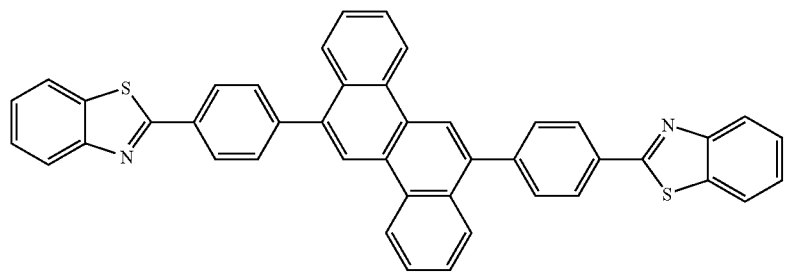
(Formula 33)
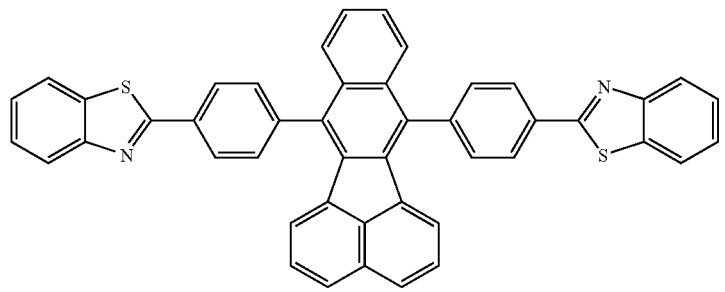
(Formula 34)

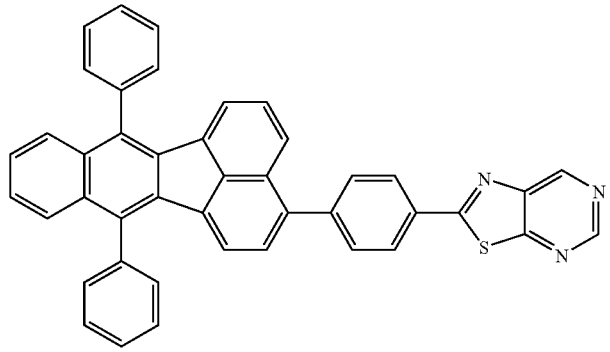

(Formula 35)

The aromatic heterocyclic compound of the present invention represented by Formula 1 may be synthesized using a conventional organic synthesis method.

The aromatic heterocyclic compound represented by Formula 1 as previously described may be included in an organic layer of an organic light-emitting diode (OLED), according to an embodiment of the present invention. Therefore, the OLED of the present invention includes a first electrode, a second electrode, and an organic layer interposed between the first electrode and the second electrode, wherein the organic layer includes an aromatic heterocyclic compound represented by Formula 1 as previously described.

Here, the organic layer may be an emission layer, a hole injection layer a hole blocking layer, an electron transport layer or a hole transport layer.

The organic layer including the aromatic heterocyclic compound represented by Formula 1 as previously described may be formed using a variety of conventional methods. In this regard, the organic layer may be formed using a vacuum deposition method or a solution deposition method such as spin coating, inkjet printing, screen printing, casting, Langmuir-Blodgeft (LB) deposition, or spray-printing. Moreover, after forming the organic layer including the aromatic heterocyclic compound represented by Formula 1 on a donor film using a vacuum deposition method or a solution deposition method, the organic layer may be thermal-transferred to a substrate on which the first electrode is formed, using a thermal transfer method. When a solution deposition method is used, unlike conventional OLEDs where the stability of the organic layer is decreased, the aromatic heterocyclic compound represented by Formula 1 has excellent solubility and thermal stability while capable of forming a stable organic layer. Thus, the OLED of the present invention, including the organic layer comprising the aromatic heterocyclic compound represented by Formula 1, has low driving voltage, high efficiency, and high brightness.

Figure 1B:
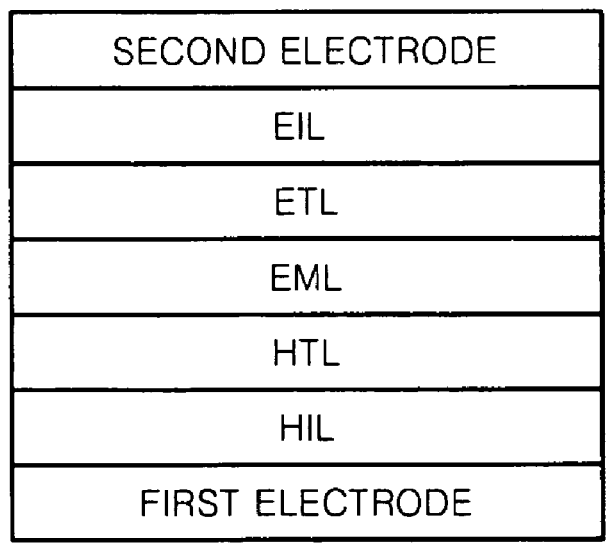
Figure 1C:
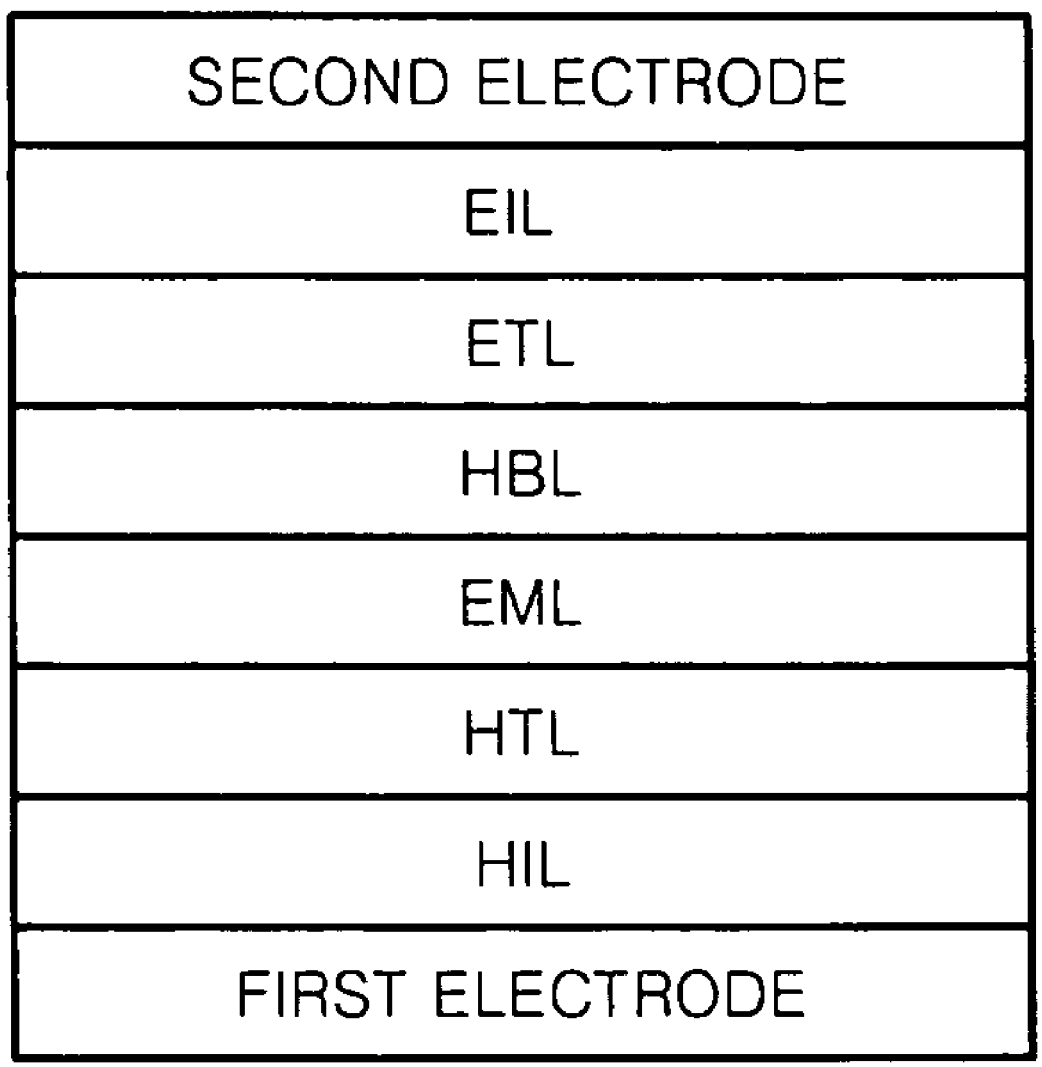

The OLED according to the present invention may further include at least one layer selected from the group consisting of a first electrode, a second electrode, a hole-injection layer, a hole transport layer, a hole blocking layer, an electron transport layer, and an electron injection layer. More specifically, FIGS. 1A, 1B, and 1C illustrate cross-sectional views of OLEDs according to embodiments of the present invention. The OLED of FIG. 1A has a first electrode/hole injection layer/hole transport layer/emission layer/electron transport layer/electron injection layer/second electrode structure, and the OLED of FIG. 1B has a first electrode/hole injection layer/hole transport layer/emission layer/electron transport layer/electron injection layer/second electrode structure. In addition, the OLED of FIG. 1C has a first electrode/hole injection layer/hole transport layer/emission layer/hole blocking layer/electron transport layer/electron injection layer/second electrode structure. Here, at least one of the emission layer, hole injection layer, hole transport layer, hole blocking layer, and electron transport layer may include an aromatic heterocyclic compound represented by Formula 1.

Hereinafter, a method of manufacturing an OLED according to an embodiment of the present invention will be described with reference to the OLED illustrated in FIG. 1C.

First, a material for a first electrode with a high work function is formed on a substrate using a vapor deposition or sputtering method to form a first electrode. A transparent and highly conductive material such as indium tin oxide (ITO), indium zinc oxide (IZO), tin oxide ($SnO_2$), and zinc oxide (ZnO) may be used as the material for the first electrode. The first electrode may be an anode. Here, the substrate may be a substrate conventionally used for OLEDs, and may preferably be a glass or a transparent plastic substrate with excellent mechanical strength, thermostability, transparency, surface flatness, ease of treatment, and water resistance.

Next, a hole injection layer (HIL) may be formed on the first electrode using a method such as vacuum deposition, spin coating, casting, or LB deposition.

When the HIL is formed by vacuum deposition, the deposition conditions vary depending on a compound used as a material for the HIL, the structure of the HIL to be formed, and thermal properties. Typically however, it is desirable to select deposition conditions appropriately within the ranges of a deposition temperature of 100 to 500° C., vacuum degree of $10^{-8}$ to $10^{-3}$ torr, and deposition speed of 0.01 to 100 Å/sec.

When forming the HIL by spin coating, the coating conditions vary depending on a compound used as a material for the HIL, structure of the HIL to be formed, and thermal properties. Typically however, it is desirable to select appropriately a coating speed within the range of approximately 2000 to 5000 rpm, and a temperature of thermal treatment for removing a solvent after coating within the range of 80 to 200° C.

The HIL material may be an aromatic heterocyclic compound represented by Formula 1 as previously described. Alternatively, the HIL material may be a conventional hole injection material. For example, the conventional hole injection material may be a phthalocyanine compound such as copper phthalocyanine or starburst-type amine derivatives such as TCTA, m-MTDATA, m-MTDAPB, soluble condutive polymer such as Pani/DBSA (Polyaniline/Dodecylbenzenesulfonic acid) or PEDOT/PSS (Poly(3,4-ethylenedioxythiophene)/Poly(4-styrenesulfonate), Pani/CSA (Polyaniline/Camphor sulfonicacid), and PANI/PSS (Polyaniline/Poly 4-styrenesulfonate) disclosed in U.S. Pat. No. 4,356,429.

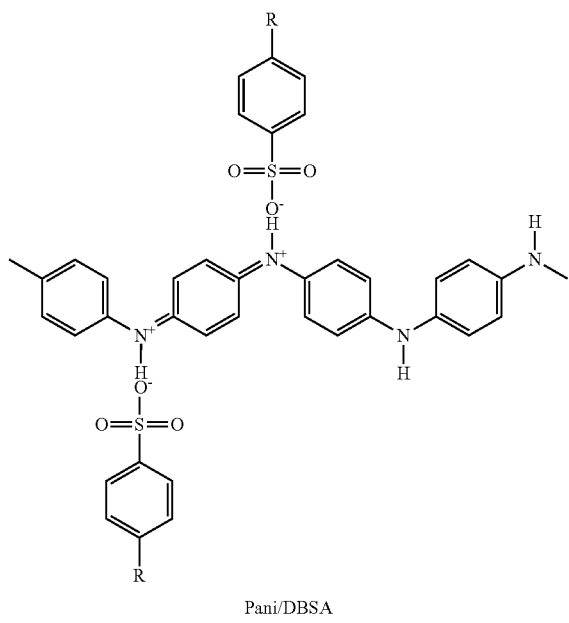

Pani/DBSA

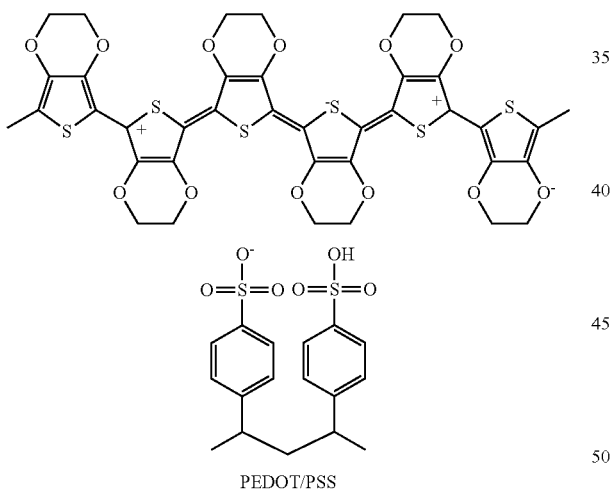

PEDOT/PSS

The thickness of the HIL may be 100 to 10000 Å, and preferably 100 to 1000 Å. If the thickness of the HIL is within the above range, a satisfactory hole injection characteristic can be obtained without a substantial decline in the driving voltage.

Next, a hole transport layer (HTL) may be formed on the HIL using a method such as vacuum deposition, spin coating, casting, or LB deposition. When the HTL is formed by vacuum deposition or spin coating, the deposition or coating conditions differ according to the compound used, but typically, are selected from ranges very similar to those for forming the HIL The HTL material may be an aromatic heterocyclic compound represented by Formula 1 as previously described. Alternatively, the HTL material may be a conventional hole transport material such as carbazole derivatives including N-phenylcarbazole and polyvinylcarbazole and conventional amine derivatives having an aromatic condensed ring such as, N,N'-bis(3-methylphenyl)-N,N'-diphenyl-[1,1-biphenyl]-4,4'-diamine (TPD) and N,N'-di(naphthalen-1-yl)-N,N'-diphenyl benzidine (α-NPD).

The thickness of the HTL may be 50 to 1000 Å, and preferably 100 to 800 Å. If the thickness of the HTL is within the above range, a satisfactory hole transport characteristic can be obtained without a substantial decline in the driving voltage.

An emission layer (EML) may be formed on the HTL using a method such as vacuum deposition, spin coating, casting, or LB deposition. If the EML is formed using vacuum deposition or spin coating, the deposition conditions vary depending on the compound used, but typically, are selected from the ranges very similar to those for forming the HIL.

The EML material may be an aromatic heterocyclic compound represented by Formula 1 as previously described. Here, the aromatic heterocyclic compound of Formula 1 may be used as a dopant, and may be used together with an appropriate conventional host material, and the EML material may further include a conventional dopant material. Moreover, the aromatic heterocyclic compound of Formula 1 may be used as a host. Meanwhile, the aromatic heterocyclic compound of Formula 1 may be used by itself. The host material may be Alq3, CBP (4,4'-N,N'-dicarbazole-biphenyl) or PVK (poly (n-vinylcarbazole)), 9,10-di(naphthalen-2-yl)anthracene (ADN), but is not limited thereto.

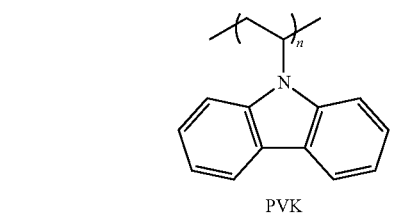

PVK

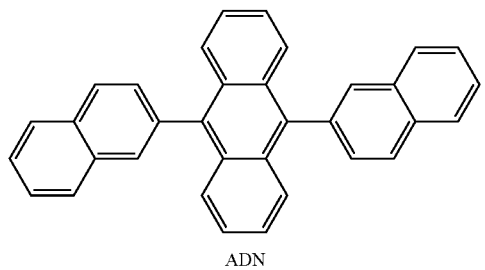

ADN

Meanwhile, a conventional red dopant such as PtOEP, Ir(piq)$_3$, Btp$_2$Ir(acac), DCJTB or the like may be used, but is not limited thereto.

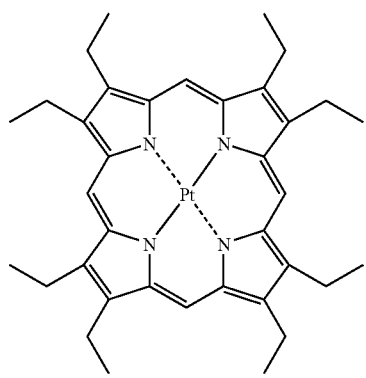

PtOEP

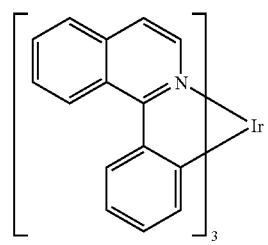

Ir(piq)₃

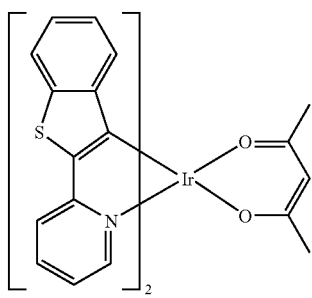

Btp₂Ir(acac)

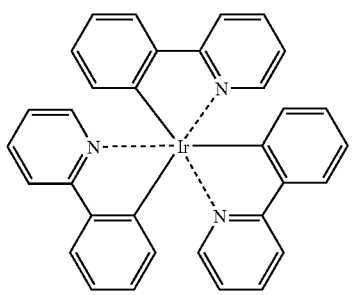

Ir(ppy)₃

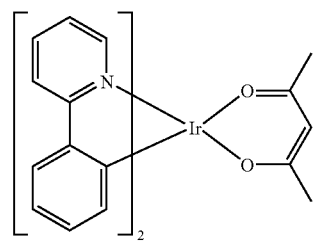

Ir(ppy)₂(acac)

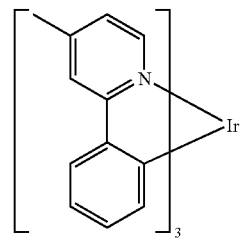

Ir(mpyp)₃

Moreover, a conventional green dopant such as Ir(ppy)₃ (ppy=phenylpyridine), Ir(ppy)₂(acac), Ir(mpyp)₃, C545T or the like may be used, but is not limited thereto.

Meanwhile, a conventional blue dopant such as F₂Irpic, (F₂ppy)₂Ir(tmd), Ir(dfppz)₃, ter-fluorene, 4,4'-bis(4-diphenylaminostyrile) biphenyl (DPAVBi), 2,5,8,11-tetra-t-butyl perylene (TBP) or the like may be used, but is not limited thereto.

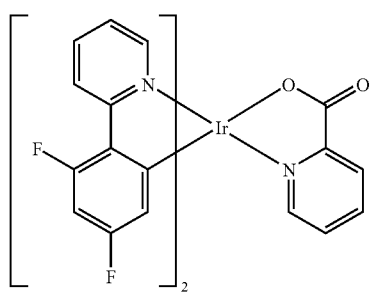

F₂Irpic

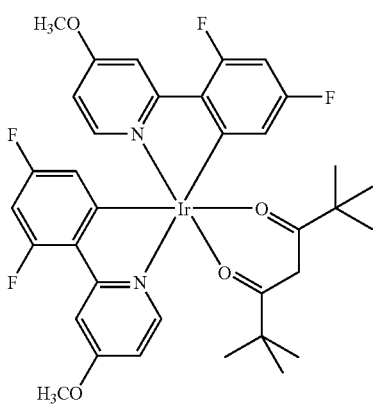

(F₂ppy)₂Ir(tmd)

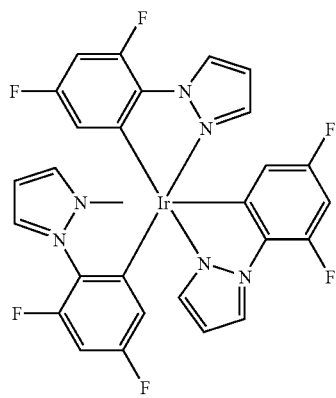

Ir(dfppz)₃

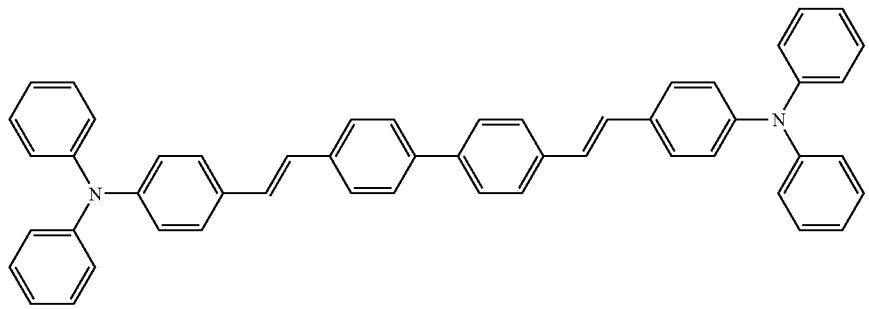

DPAVBi

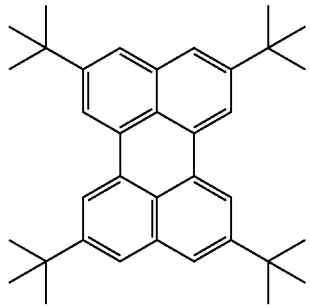

TBP

In the case where the dopant and the host are used together, the doping concentration of the dopant is not particularly limited, but the dopant content may conventionally be 0.01 to 15 parts by weight based on 100 parts by weight of the host.

The thickness of the EML may be 100 to 1000 Å, and preferably 200 to 600 Å. If the thickness of the EML is within the above range, an excellent emission characteristic can be obtained without a substantial decline in the driving voltage.

In the case where a phosphorescent dopant is included in the EML material, in order to prevent triplet excitrons or holes from diffusing into the electron transport layer, a hole blocking layer (HBL) may be formed between the HTL and the EML using a method such as vacuum deposition, spin coating, casting, or LB deposition. When the HBL is formed by vacuum deposition or spin coating, the conditions vary depending on the compound used, but are typically selected from condition ranges very similar to those for forming the HIL.

The HBL material may the aromatic heterocyclic compound of Formula 1 as previously described. Alternatively, a conventional HBL may be used, examples of which include oxadiazole derivatives, triazole derivatives, and phenanthroline derivatives.

The thickness of the HBL may be approximately 50 to 1000 Å, and preferably 100 to 300 Å. If the thickness of the HBL is within the above range, an excellent hole blocking characteristic can be obtained without a substantial decline in the driving voltage.

Next, an electron transport layer (ETL) may be formed using a method such as vacuum deposition, spin coating, casting, or LB deposition. When the ETL is formed by vacuum deposition or spin coating, the conditions vary depending on the compound used, but are typically selected from condition ranges very similar to those for forming the HIL. An ETL material has a function of stably transporting electrons injected from the cathode, and the aromatic heterocyclic compound represented by Formula 1 as previously described may be used. Alternatively, conventional electron transport materials such as quinoline derivatives, particularly tris(8-quinolinolate)aluminum (Alq3), TAZ, and Balq may be used as the ETL material, but the present invention is not limited thereto.

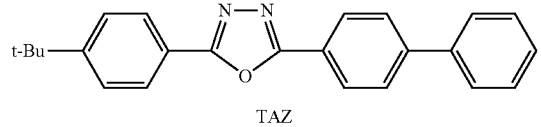

TAZ

The thickness of the ETL may be approximately 100 to 1000 Å, and preferably 150 to 500 Å. If the thickness of the ETL is within the above range, an excellent electron transporting characteristic can be obtained without a substantial decline in the driving voltage.

Moreover, an electron injection layer (EIL), which has a function of facilitating injection of electrons from the cathode, may be deposited on the ETL. The material used to form the EIL is not particularly limited and may be the aromatic heterocyclic compound of Formula 1 as previously described. Alternatively, conventional arbitrary materials for forming electron injection layers such as LiF, NaCl, CsF, Li2O, and BaO may be used. The deposition conditions of the EIL differ depending on the compound used, but are typically selected from condition ranges very similar to those for forming the HIL.

The thickness of the EIL may be approximately 1 to 100 Å, and preferably 5 to 50 Å. If the thickness of the EIL is within the above range, an excellent electron injecting characteristic can be obtained without a substantial decline in the driving voltage.

Finally, a second electrode may be formed on the EIL using methods such as vacuum deposition and sputtering. The second electrode may be used as a cathode. A metal with a low work function, an alloy, an electroconductive compound or mixtures thereof may be used as a second electrode-forming metal. Specific examples of the second electrode-forming metal include lithium (Li), magnesium (Mg), aluminum (Al), aluminum-lithium (Al—Li), calcium (Ca), magnesium-indium (Mg—In), and magnesium-silver (Mg—Ag). In addition, a transparent cathode formed of ITO or IZO may be used in order to obtain a top-emission OLED.

A method of manufacturing an OLED according to an embodiment of the present invention includes forming a first electrode on a substrate; forming an organic layer comprising an aromatic heterocyclic compound of Formula 1 on the first electrode; and forming a second electrode on the organic layer. Here, the organic layer may be one of an EML, HIL, HTL, HBL, and ETL. Meanwhile, the method of manufacturing the OLED may further include forming at least one layer selected from the group consisting of a HIL, HTL, EML, HBL, ETL, and EIL.

The organic layer including the aromatic heterocyclic compound represented by Formula 1 may be formed using vacuum deposition or a solution deposition method such as spin coating, inkjet printing, screen printing method or spray printing. In addition, the organic layer including the aromatic heterocyclic compound represented by Formula 1 may be formed on a donor film using vacuum deposition or solution deposition as previously described, and a heat-transfer method. Then the organic layer may be heat-transferred to the substrate on which the first electrode is formed, using a thermal-transfer method.

Hereinafter, synthesis examples and exemplary examples of the present invention will be presented in detail. However, these examples are for illustrative purposes only and are not intended to limit the scope of the present invention.

EXAMPLES

Synthesis Example 1

Compound 1 was synthesized according to a reaction pathway of Reaction Equations 1 and 2 below:

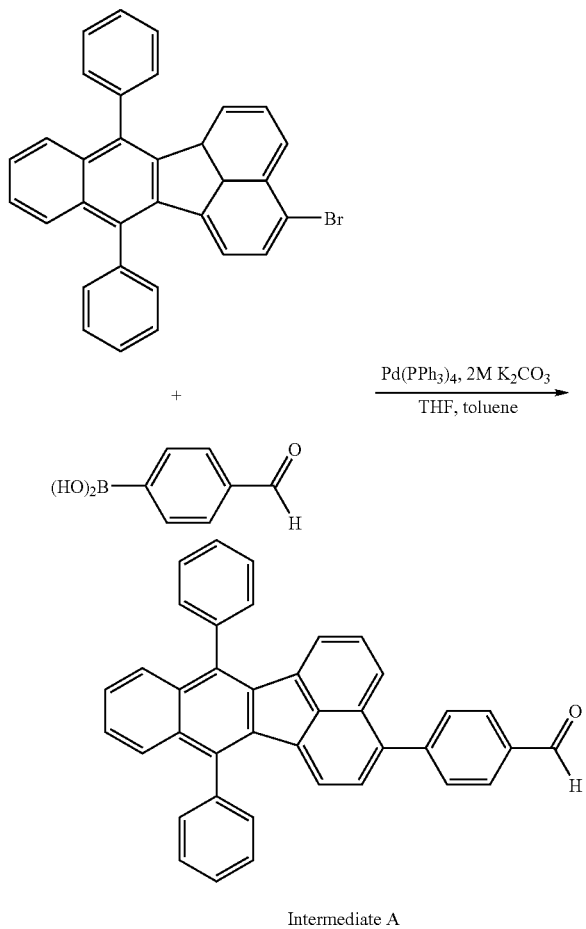

Intermediate A

Synthesis of Intermediate A 1 g of (2.1 mmol) 4-bromo-7,12-diphebenzo[k]fluorantene was dissolved in 10 ml of THF (tetrahydrofuran). Next, 310 mg (2.1 mmol) of 4-formylphenylborate, 119 mg (0.1 mmol) of tetrakis triphenyl phosphine palladium (Pd(PPh$_3$)$_4$) and 1.3 ml of 2M aqueous solution of potassium carbonate (K$_2$CO$_3$) were each dissolved in 10 ml of toluene, added to the THF mixture, and then refluxed for 24 hours. After the reaction was complete, the solvent was removed by evaporation. Next, 200 ml of ethyl acetate and 200 ml of water was each added to wash the resulting product, and an organic layer was collected and dried with anhydride magnesium sulfate. Then the resulting product was separated using silica chromatography to obtain 1.1 g of a compound (yield 93%) represented by Intermediate A above.

(Reaction Equation 2)

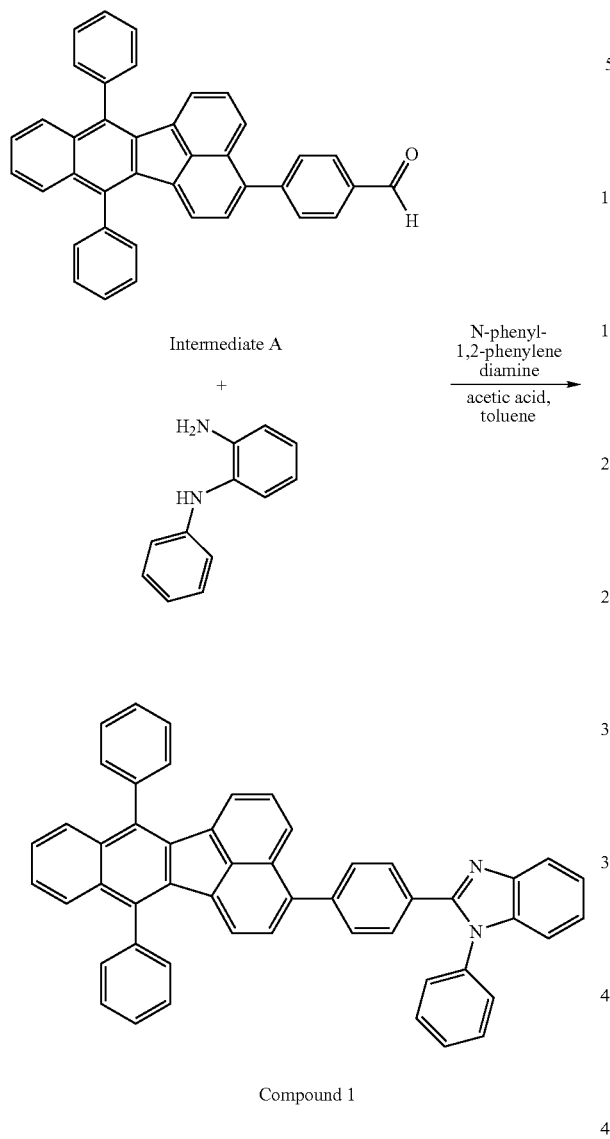

Compound 1

Synthesis Example 2

Compound 5 was synthesized according to a reaction pathway of Reaction Equations 3 and 4 below:

(Reaction Equation 3)

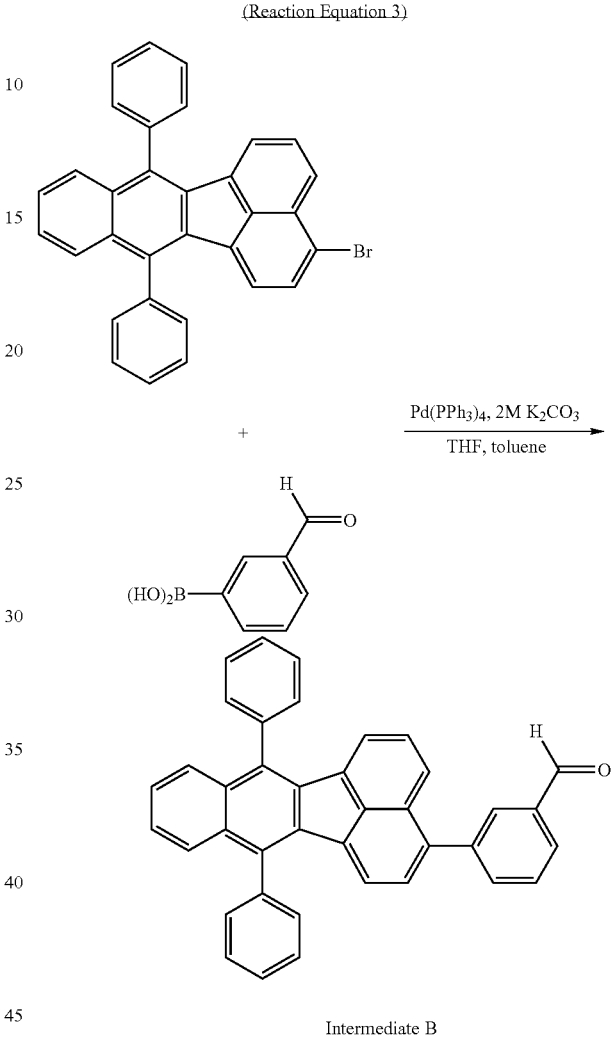

Intermediate B

Synthesis of Compound 1

Intermediate A (682 mg, 1.3 mmol) and N-phenyl-1,2-phenylenediamine (247 mg, 1.3 mmol) were added to 8 ml of toluene and 2 ml of acetic acid and refluxed for 24 hours. Next, 500 ml of ethyl acetate and 200 ml of water were each added to wash the resulting product, and an organic layer was collected and dried with anhydride magnesium sulfate. Then the resulting product was separated using silica chromatography to obtain 850 mg of a compound (yield 97%) represented by Compound 1 above.

NMR and MS analysis results of Compound 1 obtained above are as follows:

$^1$H-NMR (CDCl$_3$, 300 MHz, ppm): 7.9 (d, 1H), 7.7 (d, 1H), 7.7-7.2 (m, 28H), 6.6 (d, 2H); MS [M+H] 673

Synthesis of Intermediate B 2.5 g of (5.2 mmol) 4-bromo-7,12-diphebenzo[k]fluorantene was dissolved in 20 ml of THF (tetrahydrofuran). Next, 778 mg (5.2 mmol) of 3-formylphenylborate, 300 mg (0.26 mmol) of tetrakis triphenyl phosphine palladium (Pd(PPh$_3$)$_4$) and 3.2 ml of 2M aqueous solution of potassium carbonate (K$_2$CO$_3$) were each dissolved in 20 ml of toluene, added to the THF mixture, and then refluxed for 24 hours. After the reaction was complete, the solvent was removed by evaporation. Next, 500 ml of ethyl acetate and 500 ml of water were each added to wash the resulting product, and an organic layer was collected and dried with anhydride magnesium sulfate. Then the resulting product was separated using silica chromatography to obtain 1.2 g of a compound (yield 34%) represented by Intermediate B above.

Synthesis Example 3

Compound 9 was synthesized according to a reaction pathway of Reaction Equations 5 and 6 below:

(Reaction Equation 4)

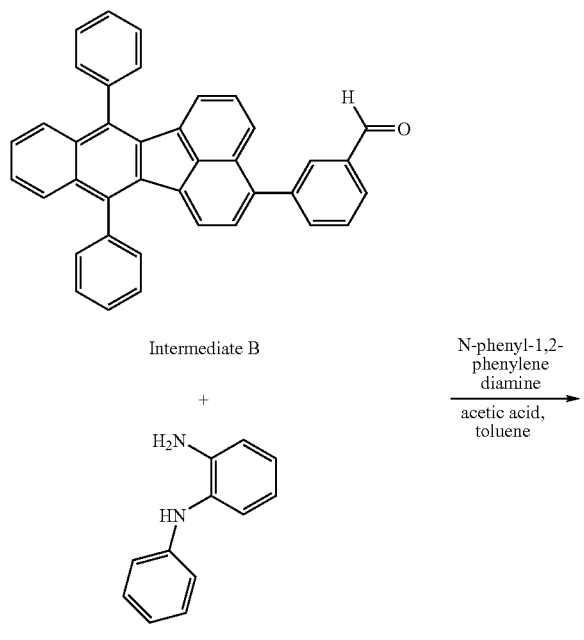

Intermediate B

+

N-phenyl-1,2-phenylenediamine
acetic acid, toluene
→

(Reaction Equation 5)

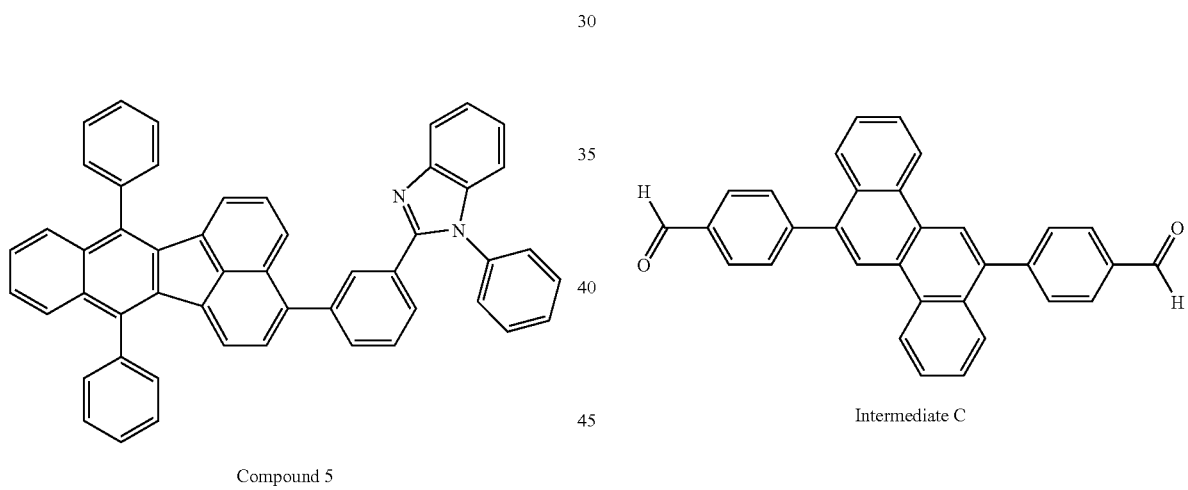

Compound 5

Synthesis of Compound 5

Intermediate B (937 mg, 1.8 mmol) and N-phenyl-1,2-phenylenediamine (340 mg, 1.3 mmol) were added to 12 ml of toluene and 2 ml of acetic acid and refluxed for 24 hours. Next, each 500 ml of ethyl acetate and 200 ml of water were each added to wash the resulting product, and an organic layer was collected and dried with anhydride magnesium sulfate. Then the resulting product was separated using silica chromatography to obtain 1.0 g of a compound (yield 80%) represented by Compound 5 above.

NMR and MS analysis results of Compound 5 obtained above are as follows:

$^1$H-NMR (CDCl$_3$, 300 MHz, ppm): 7.9 (d, 1H), 7.7-7.1 (m, 29H), 6.6-6.5 (m, 2H); MS [M+H] 673

Synthesis of Intermediate C 1.8 g of (4.7 mmol) 2,8-dibromochrysene was dissolved in 32 ml of THF (tetrahydrofuran). Next, 1.75 g (11.7 mmol) of 4-formylphenylborate, 269 mg (0.2 mmol) of tetrakis triphenyl phosphine palladium (Pd(PPh$_3$)$_4$) and 12 ml of 2M aqueous solution of potassium carbonate (K$_2$CO$_3$) were each dissolved in 16 ml of toluene, added to the THF mixture, and then refluxed for 24 hours. Next, the resulting product was cooled to room temperature, and the obtained solid was filtered and washed with ethanol and ether to obtain 1.9 g of a compound (yield 93%) represented by Intermediate C above.

(Reaction Equation 6)

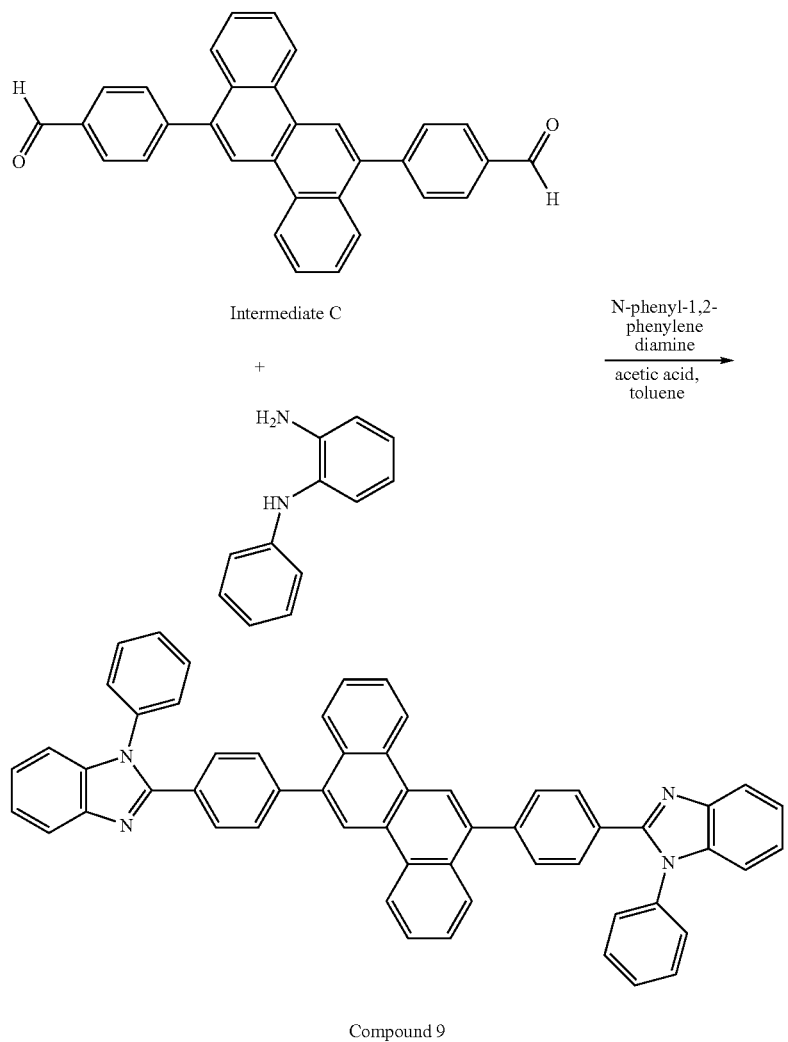

Synthesis of Compound 9

Intermediate C (1.0 g, 2.3 mmol) and N-phenyl-1,2-phenylenediamine (848 mg, 4.6 mmol) were added to 12 ml of toluene and 2 ml of acetic acid and refluxed for 24 hours. Next, each 500 ml of ethyl acetate and 500 ml of water were each added to wash the resulting product, and an organic layer was collected and dried with anhydride magnesium sulfate. Then the resulting product was separated using silica chromatography to obtain 700 mg of a compound (yield 43%) represented by Compound 9 above.

NMR and MS analysis results of Compound 9 obtained above are as follows:

$^1$H-NMR (CDCl$_3$, 300 MHz, ppm): 8.8 (d, 2H), 8.6 (s, 2H), 8.0-7.3 (m, 32H); MS [M+H] 765

Evaluation Example 1

Evaluation of Emission Characteristic of Compound (Solution Conditions)

Figure 2:
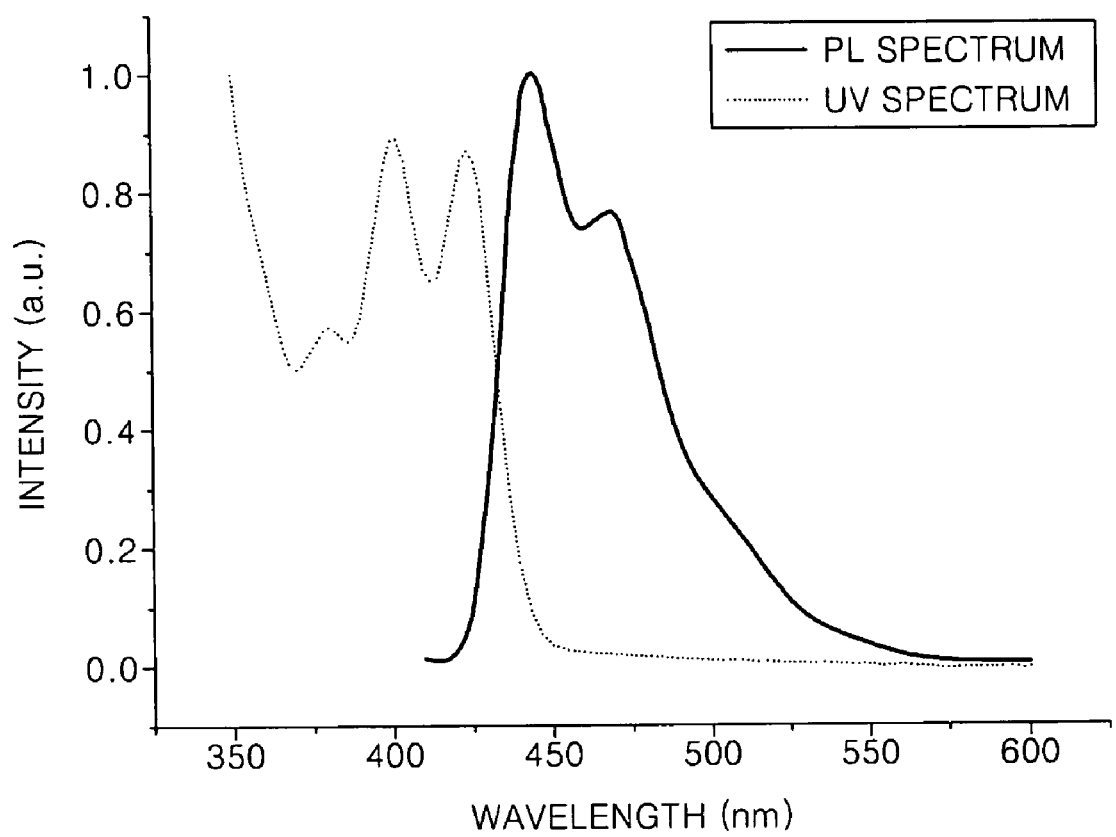
FIG. 2 is a graph illustrating a UV absorption spectrum and photoluminescence (PL) spectrum of Compound 1, according to an embodiment of the present invention.
Figure 3:
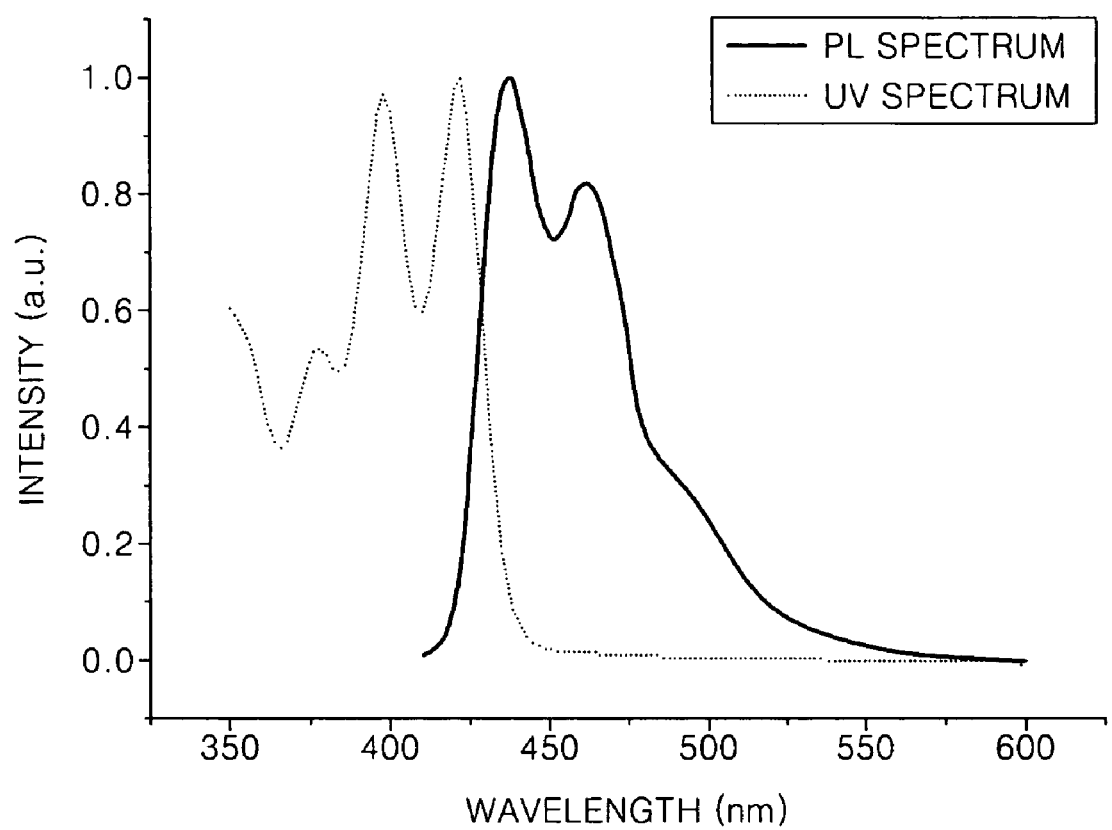
FIG. 3 is a graph illustrating a UV absorption spectrum and photoluminescence (PL) spectrum of Compound 5, according to another embodiment of the present invention.

By observing the UV absorption spectrum and PL (photoluminescence) spectrum of Compounds 1, 5, and 9, the emission characteristic of each compound was evaluated. First, Compound 1 was diluted with toluene to a concentration of 0.2 mM, and its UV absorption spectrum was measured using Shimadzu UV-350 Spectrometer. The same process was repeated for Compounds 5 and 9. Meanwhile, Compound 1 was diluted with toluene to a concentration of 10 mM, and its PL spectrum was measured using an ISC PC1 Spectrofluorometer with a xenon lamp installed therein. The same process was repeated for Compounds 5 and 9. The results are shown in Table 1 below. FIGS. 2 and 3 are graphs showing the UV spectra and PL spectra of Compounds 1 and 5.

TABLE 1

| Compound No. | Absorption Wavelength (nm) | PL Wavelength (nm) |
|---|---|---|
| 1 | 402 | 445 |
| 5 | 398 | 437 |
| 9 | 302 | 425 |

Example 1

Using Compound 1 as a material for an electron transport layer, an organic light-emitting diode having the following structure was manufactured:

ITO/α-NPD(750 Å)/DPAVBi (5 wt %)+ADN (350 Å)/Compound 1(180 Å)/LiF(10 Å)/Al(2000 Å).

The anode was prepared by cutting an ITO glass substrate of 15 Ω/cm$^2$ (1000 Å) to a size of 50 mm×50 mm×0.7 mm, sonicating in acetone, isopropyl alcohol and deionized water for 15 minutes each, and UV ozone cleaning for 30 minutes. α-NPD was vacuum deposited on the ITO anode at a deposition speed of 1 Å/sec to a thickness of 750 Å to form a hole transport layer, then DPAVBi (4,4'-bis(4-diphenylaminostarile)biphenyl) and ADN (9,10-di(naphthalen-2-yl)anthracene were each vacuum deposited on the hole transport layer at deposition speeds of 5 Å/sec and 30 Å/sec, respectively, to a thickness of 350 Å to form an emission layer (with a DPAVBi content of 5 wt %). Next, Compound 1 was vacuum-deposited on the emission layer to a thickness of 180 Å to form an electron transport layer, and LiF for an electron injection layer and Al for a cathode were respectively vacuum deposited on the electron transport layer to thicknesses of 10 Å and 2000 Å, to produce an OLED as illustrated in FIG. 1A, and referred to as Sample 1.

Example 2

An OLED was manufactured using the same method in Example 1, except that Compound 5 was used instead of Compound 1 in Example 1. The OLED is referred to as Sample 2.

Example 3

An OLED was manufactured using the same method in Example 1, except that Compound 9 was used instead of Compound 1 in Example 1. The OLED is referred to as Sample 3.

Comparative Example 1

An OLED was manufactured using the same method in Example 1, except that Alq3 was used instead of Compound 1 in Example 1. The OLED is referred to as Sample A.

Evaluation Example 2

Driving voltages, current densities, and brightness of Samples 1 to 3 and A were each measured using a PR650 (Spectroscan) Source Measurement Unit, with the results shown in Table 2 below:

TABLE 2

| Sample No. | Turn on Driving voltage (V) | Current Density at 1000 cd/m$^2$ (mA/cm$^2$) | Voltage at 1000 cd/m$^2$ (V) |
|---|---|---|---|
| 1 | 3.4 | 24 | 5.6 |
| 2 | 3.4 | 22 | 5.8 |
| 3 | 3.6 | 20 | 6.0 |
| A | 3.8 | 15 | 8.0 |

Example 4

Using Compound 1 as a dopant of the emission layer and ADN as a host of the emission layer, an OLED having the structure below was manufactured:

ITO/α-NPD(750 Å)/Compound 1 (5 wt %)+ADN(350 Å)/Alq3(180 Å)/LiF(10 Å)/Al(2000 Å).

The anode was prepared by cutting an ITO glass substrate of 15 Ω/cm$^2$ (1000 Å) to a size of 50 mm×50 mm×0.7 mm, sonicating in acetone, isopropyl alcohol and deionized water for 15 minutes each, and UV ozone cleaning for 30 minutes. α-NPD was vacuum deposited on the ITO anode at a deposition speed of 1 Å/sec to a thickness of 750 Å to form a hole transport layer. Then Compound 1 and ADN (9,10-di(naphthalen-2-yl)anthracene were each vacuum deposited on the hole transport layer at deposition speeds of 5 Å/sec and 30 Å/sec, respectively, to a thickness of 350 Å to form an emission layer. Next, Alq3 was vacuum-deposited on the emission layer to a thickness of 180 Å to form an electron transport layer. Next, LiF for an electron injection layer and Al for a cathode were respectively vacuum deposited on the electron transport layer to thicknesses of 10 Å and 2000 Å, respectively, to produce an OLED as illustrated in FIG. 1A, and referred to as Sample 4.

Example 5

An OLED was manufactured using the same method in Example 4, except that Compound 5 was used instead of Compound 1 in Example 4. The OLED is referred to as Sample 5.

Example 6

An OLED was manufactured using the same method in Example 4, except that Compound 9 was used instead of Compound 1 in Example 4. The OLED is referred to as Sample 6.

Evaluation Example 3

Figure 4:
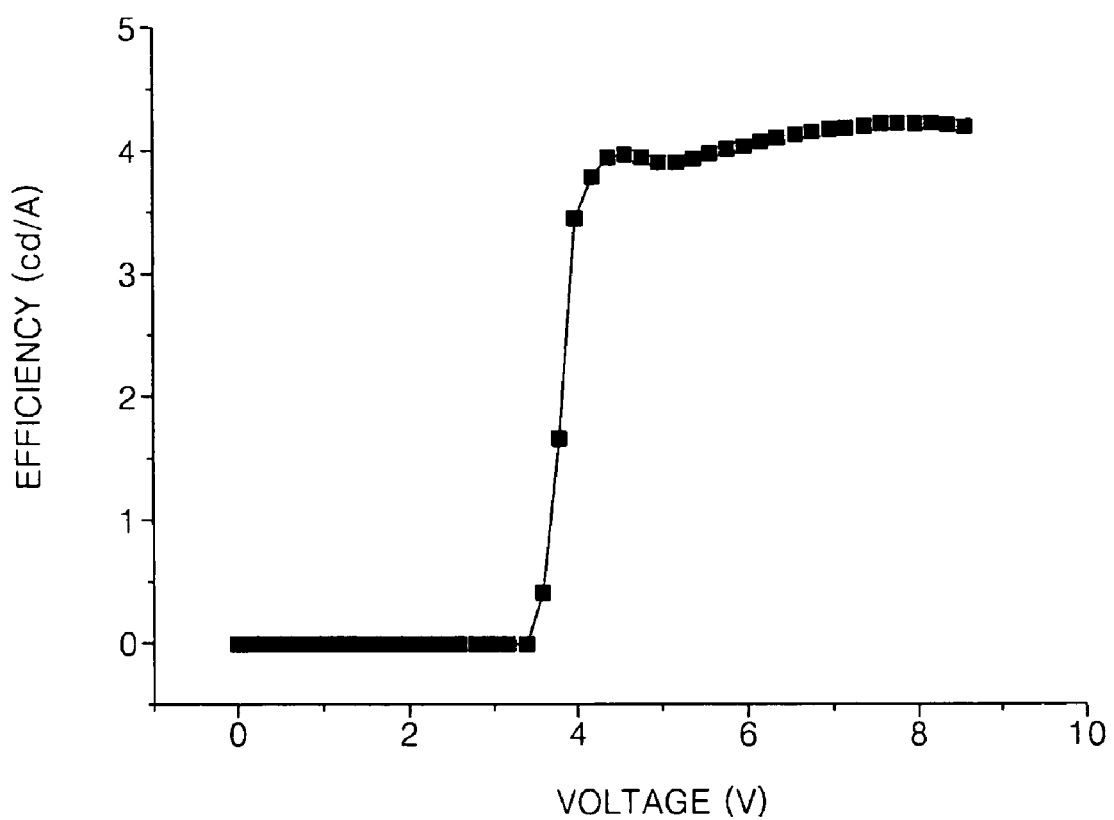
FIG. 4 is a graph illustrating a voltage-efficiency characteristic of an organic light-emitting diode according to another embodiment of the present invention.

Driving voltages, current densities, and brightness of Samples 1 to 3 and A were each measured using a PR650 (Spectroscan) Source Measurement Unit, with the results shown in Table 3 below. FIG. 4 is a graph illustrating a voltage-efficiency characteristic of Sample 4.

TABLE 3

| Sample No. | Turn on Driving voltage (V) | Maximum Efficiency (cd/A) | Voltage at 1000 cd/m$^2$ (V) |
|---|---|---|---|
| 4 | 3.6 | 4.24 | 7.8 |
| 5 | 3.8 | 2.82 | 7.4 |
| 6 | 3.8 | 1.90 | 7.6 |

The aromatic heterocyclic compound represented by Formula 1 as previously described has excellent light-emitting characteristic, and an organic light-emitting diode including an organic layer comprising the aromatic heterocyclic compound is capable of achieving low driving voltage, high brightness, high efficiency, high color purity, and long life span.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An aromatic heterocyclic compound represented by Formula 1 below:

(Formula 1)

wherein A is one of substituted or unsubstituted benzo[k]fluoranthene or substituted or unsubstituted chrysene;
$Ar_1$ is substituted or unsubstituted $C_5$-$C_{12}$ arylene group,
n is an integer in the range of 0 to 6,
$Ar_2$ is a terminal group of Formula 2 below;
m is an integer in the range of 1 to 6; and
k is an integer in the range of 2 to 4:

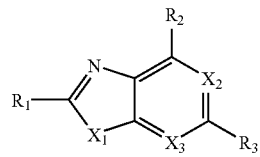
(Formula 2)

wherein $X_1$ is $N(R_4)$;
$X_2$ and $X_3$ are each $C(R_5)$; and
at least one of $R_1$ to $R_5$ is a linkage site to A or $Ar_1$ of Formula 1 above, and the remaining groups of $R_1$ to $R_5$ that are not linkage sites to A or $Ar_1$ are each independently one selected from the group consisting of hydrogen, halogen, cyano group, nitro group, hydroxyl group, substituted or unsubstituted $C_1$-$C_{20}$ alkyl group, substituted or unsubstituted $C_2$-$C_{20}$ alkenyl group, substituted or unsubstituted $C_2$-$C_{20}$ alkynyl group, substituted or unsubstituted $C_5$-$C_{20}$ cycloalkyl group, substituted or unsubstituted $C_5$-$C_{20}$ cycloalkenyl group, substituted or unsubstituted $C_5$-$C_{20}$ aryl group, substituted or unsubstituted $C_2$-$C_{30}$ heteroaryl group, and a group represented by —$N(Z_1)(Z_2)$, wherein $Z_1$ and $Z_2$ are each independently one of hydrogen, substituted or unsubstituted $C_1$-$C_{20}$ alkyl group, or substituted or unsubstituted $C_5$-$C_{20}$ aryl group.

2. An aromatic heterocyclic compound of claim 1, represented by Formula 1a below:

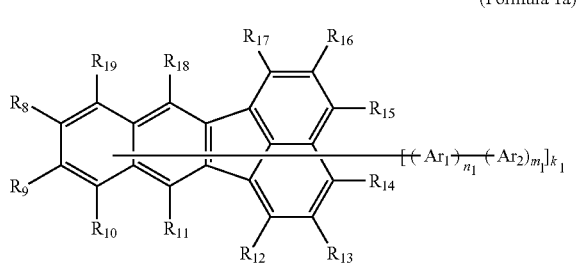
(Formula 1a)

wherein $k_1$ is the number of linkage sites to $Ar_1$ among $R_8$ to $R_{19}$;
the remaining groups of $R_8$ to $R_{19}$ that are not linkage sites to $Ar_1$ are each independently one selected from the group consisting of hydrogen, halogen, cyano group, nitro group, hydroxyl group, substituted or unsubstituted $C_1$-$C_{20}$ alkyl group, substituted or unsubstituted $C_2$-$C_{20}$ alkenyl group, substituted or unsubstituted $C_2$-$C_{20}$ alkynyl group, substituted or unsubstituted $C_5$-$C_{20}$ cycloalkyl group, substituted or unsubstituted $C_5$-$C_{20}$ cycloalkenyl group, substituted or unsubstituted $C_5$-$C_{20}$ aryl group, substituted or unsubstituted $C_2$-$C_{30}$ heteroaryl group, and a group represented by —$N(Z_1)(Z_2)$ wherein $Z_1$ and $Z_2$ are each independently one of hydrogen, substituted or unsubstituted $C_1$-$C_{20}$ alkyl group, or substituted or unsubstituted $C_5$-$C_{20}$ aryl group;
$Ar_1$ is a substituted or unsubstituted $C_5$-$C_{12}$ arylene group;
$n_1$ is an integer in the range of 1 to 6;
$Ar_2$ is a terminal group of Formula 2 below;
$m_1$ is an integer in the range of 1 to 6; and
$k_1$ is an integer in the range of 2 to 4;

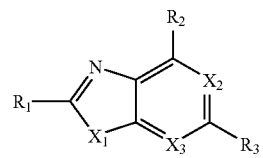
(Formula 2)

wherein $X_1$ is $N(R_4)$;
$X_2$ and $X_3$ are $C(R_5)$; and
at least one of $R_1$ to $R_5$ is a linkage site to A or $Ar_1$ of Formula 1a above, and the remaining groups of $R_1$ to $R_5$ that are not linkage sites to A or $Ar_1$ are each independently one selected from the group consisting of hydrogen, halogen, cyano group, nitro group, hydroxyl group, substituted or unsubstituted. $C_1$-$C_{20}$ alkyl group, substituted or unsubstituted $C_2$-$C_{20}$ alkenyl group, substituted or unsubstituted $C_2$-$C_{20}$ alkynyl group, substituted or unsubstituted $C_5$-$C_{20}$ cycloalkyl group, substituted or unsubstituted $C_5$-$C_{20}$ cycloalkenyl group, substituted or unsubstituted $C_5$-$C_{20}$ aryl group, substituted or unsubstituted $C_2$-$C_{30}$ heteroaryl group, and a group represented by —$N(Z_1)(Z_2)$, wherein $Z_1$ and $Z_2$ are each independently one of hydrogen, substituted or unsubstituted $C_1$-$C_{20}$ alkyl group, or substituted or unsubstituted $C_5$-$C_{20}$ aryl group.

3. An aromatic heterocyclic compound of claim 2, wherein k is the number of linkage sites to $Ar_1$ among $R_8$ to $R_{19}$, and the remaining groups that are not linkage sites to $Ar_1$ among $R_8$ to $R_{19}$ are each independently selected from the group consisting of hydrogen, halogen, cyano group, nitro group, hydroxyl group, substituted or unsubstituted $C_1$-$C_{10}$ alkyl group, substituted or unsubstituted $C_5$-$C_{14}$ aryl group, and substituted or unsubstituted $C_2$-$C_{14}$ heteroaryl group.

4. An aromatic heterocyclic compound of claim 2, wherein at least one of $R_{11}$, $R_{14}$, $R_{15}$ and $R_{18}$ is a linkage site to $Ar_1$.

5. An aromatic heterocyclic compound of claim 1, represented by, Formula 1b below:

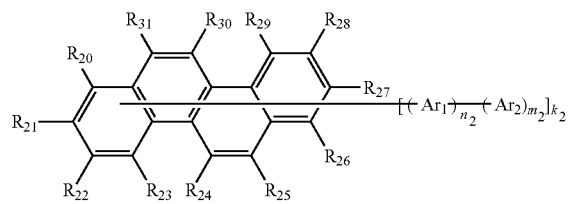
(Formula 1b)

wherein among $R_{20}$ to $R_{31}$, $k_2$ is the number of linkage sites to one of $Ar_1$ or $Ar_2$;

the remaining groups among $R_{20}$ to $R_{31}$ that are not linkage sites to $Ar_1$ or $Ar_2$ are each independently one selected from the group consisting of hydrogen, halogen, cyano group, nitro group, hydroxyl group, substituted or unsubstituted $C_1$-$C_{20}$ alkyl group, substituted or unsubstituted $C_2$-$C_{20}$ alkenyl group, substituted or unsubstituted $C_2$-$C_{20}$ alkynyl group, substituted or unsubstituted $C_5$-$C_{20}$ cycloalkyl group, substituted or unsubstituted $C_5$-$C_{20}$ cycloalkenyl group, substituted or unsubstituted $C_5$-$C_{20}$ aryl group, substituted or unsubstituted $C_2$-$C_{30}$ heteroaryl group, and a group represented by —N($Z_1$)($Z_2$), wherein $Z_1$ and $Z_2$ are each independently one of hydrogen, substituted or unsubstituted $C_1$-$C_{20}$ alkyl group, or substituted or unsubstituted $C_5$-$C_{20}$ aryl group;

$Ar_1$ is a substituted or unsubstituted $C_5$-$C_{12}$ arylene group;

$n_2$ is an integer in the range of 0 to 6;

$Ar_2$ is a terminal group of Formula 2 below;

$m_2$ is an integer in the range of 1 to 6; and $k_2$ is an integer in the range of 2 to 4:

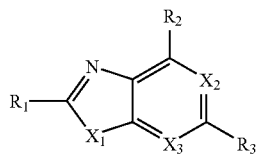

(Formula 2)

wherein $X_1$ is $N(R_4)$;

$X_2$ and $X_3$ are each $C(R_5)$; and at least one of $R_1$ to $R_5$ is a linkage site to A or $Ar_1$ of Formula 1 above, and the remaining groups of $R_1$ to $R_5$ that are not linkage sites to A or $Ar_1$ are each independently one selected from the group consisting of hydrogen, halogen, cyano group, nitro group, hydroxyl group, substituted or unsubstituted $C_1$-$C_{20}$ alkyl group, substituted or unsubstituted $C_2$-$C_{20}$ alkenyl group, substituted or unsubstituted $C_2$-$C_{20}$ alkynyl group, substituted or unsubstituted $C_5$-$C_{20}$ cycloalkyl group, substituted or unsubstituted $C_5$-$C_{20}$ cycloalkenyl group, substituted or unsubstituted $C_5$-$C_{20}$ aryl group, substituted or unsubstituted $C_2$-$C_{30}$ heteroaryl group, and a group represented by —N($Z_1$)($Z_2$), wherein $Z_1$ and $Z_2$ are each independently one of hydrogen, substituted or unsubstituted $C_1$-$C_{20}$ alkyl group, or substituted or unsubstituted $C_5$-$C_{20}$ aryl group.

6. An aromatic heterocyclic compound of claim 5, wherein $k_2$ is the number of linkage sites among $R_{20}$ to $R_{31}$ to one of $Ar_1$ or $Ar_2$, and remaining groups that are not linkage sites to one of $Ar_1$ or $Ar_2$ among $R_{20}$ to $R_{31}$ are each independently selected from the group consisting of hydrogen, halogen, cyano group, nitro group, hydroxyl group, substituted or unsubstituted $C_1$-$C_{10}$ alkyl group, substituted or unsubstituted $C_5$-$C_{14}$ aryl group, and substituted or unsubstituted $C_2$-$C_{14}$ heteroaryl group.

7. An aromatic heterocyclic compound of claim 1, wherein A is one of the structures below:

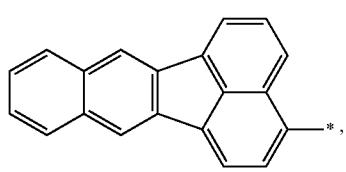

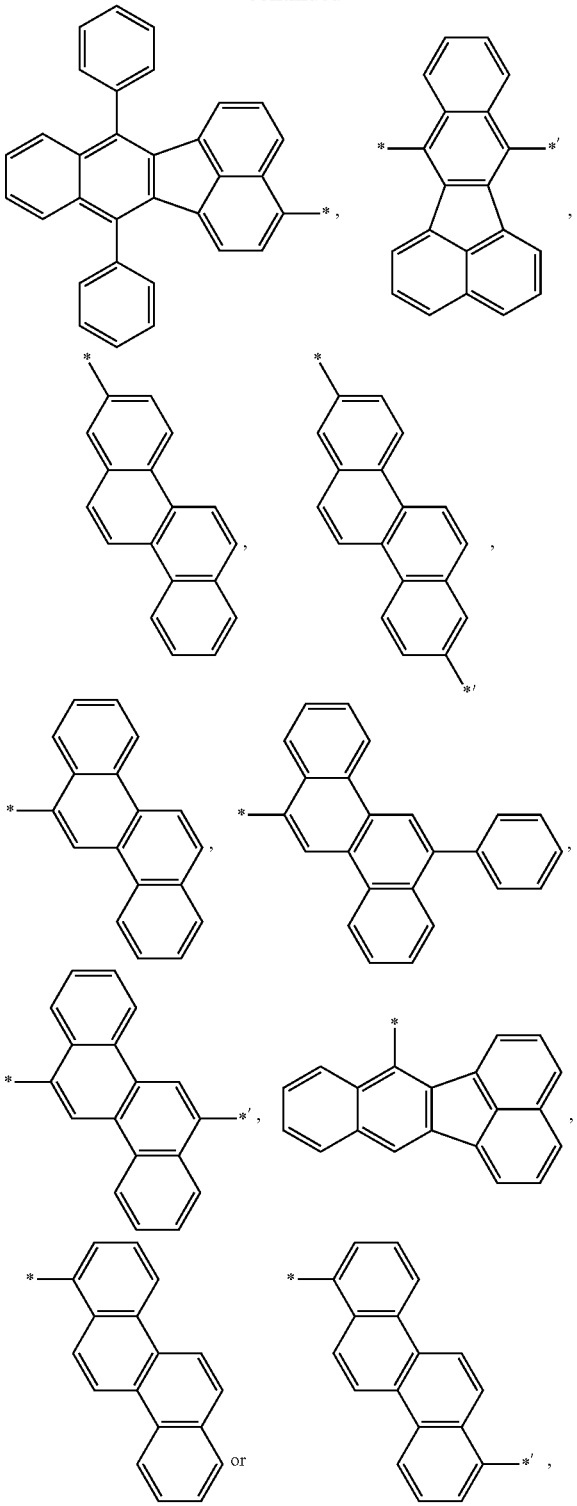

wherein * and *' each independently represent linkage sites to $Ar_1$ or $Ar_2$.

8. An aromatic heterocyclic compound of claim 1, wherein $Ar_1$ is one selected from the group consisting of phenylene, bromophenylene, chlorophenylene, fluorophenylene, cyanophenylene, $C_1$-$C_{10}$ alkylphenylene, $C_1$-$C_{10}$ alkoxyphenylene, naphthylphenylene, dinaphthylphenylene, naphthylene, bromonaphthylene, chloronaphthylene, fluoronaphthyl ene, cyanonaphthylene, $C_1$-$C_{10}$ alkylnaphthylene, $C_1$-$C_{10}$ alkoxynaphthylene, phenylnaphthylene, diphenylnaphthylene, and terphenylnaphthylene.

9. An aromatic heterocyclic compound of claim 1, wherein —$(Ar_1)_n$— is one of the structures represented below:

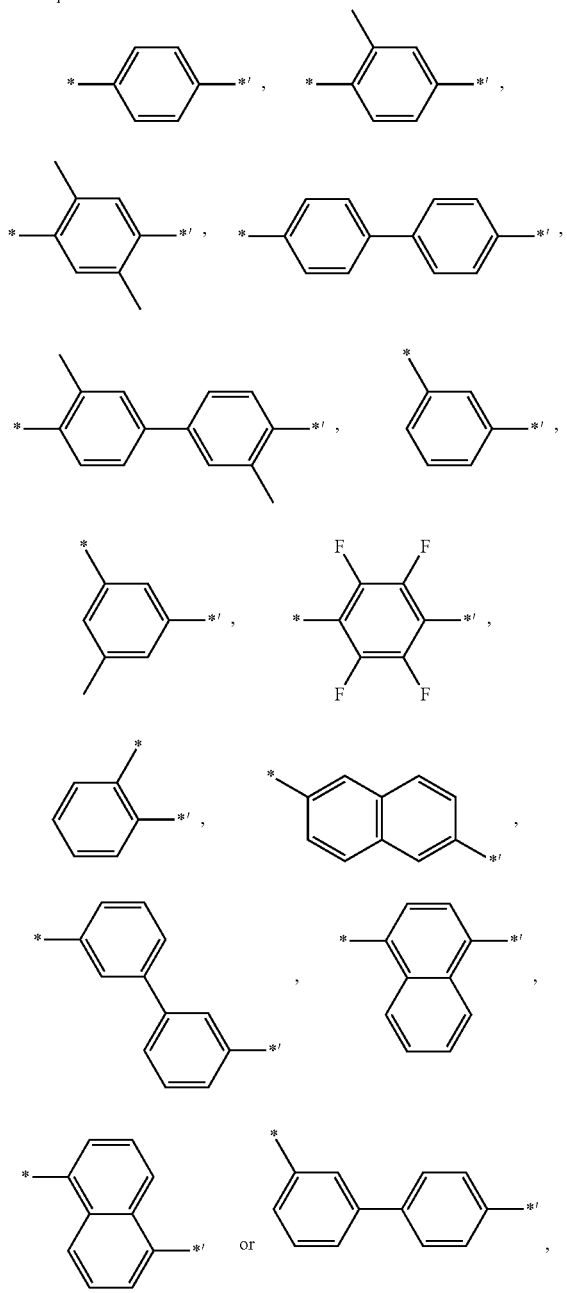

wherein * represents a linkage site to A, and *' represents a linkage site to $Ar_2$.

10. An aromatic heterocyclic compound of claim 1, wherein one of $R_1$ to $R_5$ is a linkage site to one of A or $Ar_1$, and the remaining groups of $R_1$ to $R_5$ that are not linkage sites to one of A or $Ar_1$ are each independently selected form the group consisting of hydrogen, halogen, cyano group, nitro group, hydroxyl group, substituted or unsubstituted $C_1$-$C_{10}$ alkyl group, substituted or unsubstituted $C_5$-$C_{14}$ aryl group, and substituted or unsubstituted $C_2$-$C_{14}$ heteroaryl group, and a group represented by —$N(Z_1)(Z_2)$, wherein $Z_1$ and $Z_2$ are each independently one of hydrogen, substituted or unsubstituted $C_1$-$C_{10}$ alkyl group, or substituted or unsubstituted $C_5$-$C_{14}$ aryl group.

11. An aromatic heterocyclic compound of claim 1, wherein one of $R_1$ and $R_2$ of Formula 2 is a linkage site to A or $Ar_1$.

12. An aromatic heterocyclic compound of claim 1, wherein $X_2$ and $X_3$ of Formula 2 are the same.

13. An aromatic heterocyclic compound of claim 1, wherein $Ar_2$ is one of the structures represented below:

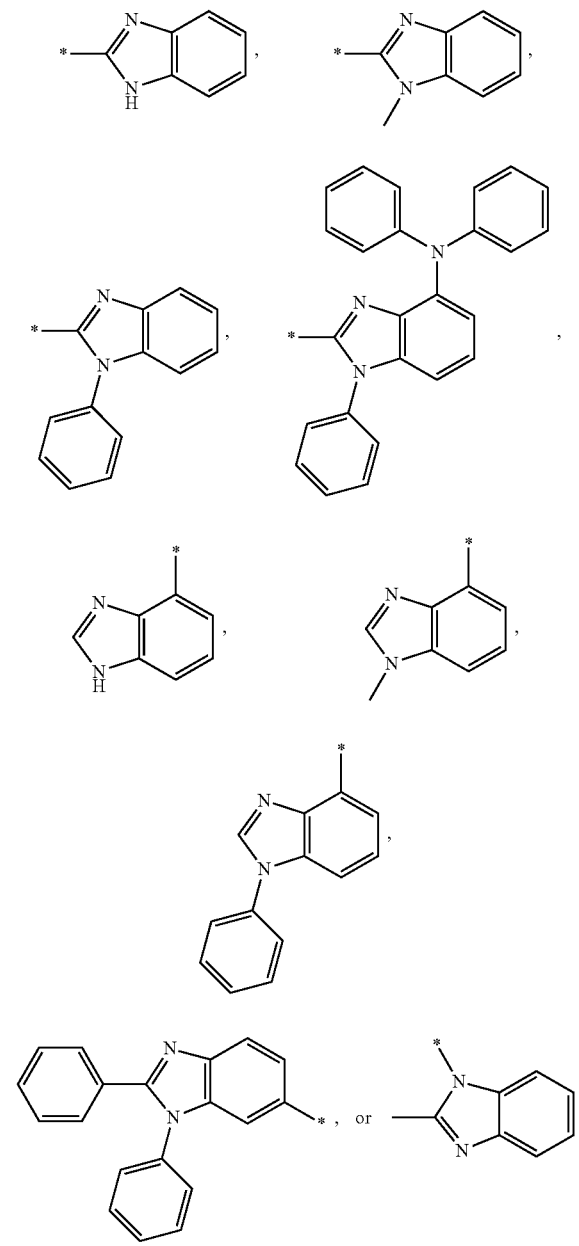

wherein * represents a linkage site to $Ar_1$.

14. The aromatic heterocyclic compound of claim 1, represented by one of the formulae represented below:
(Formula 7)
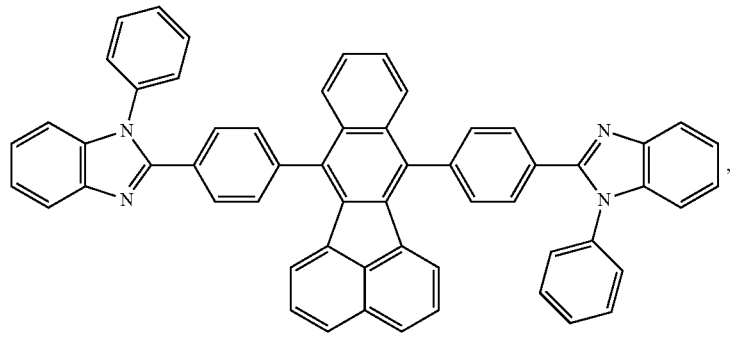
(Formula 8)
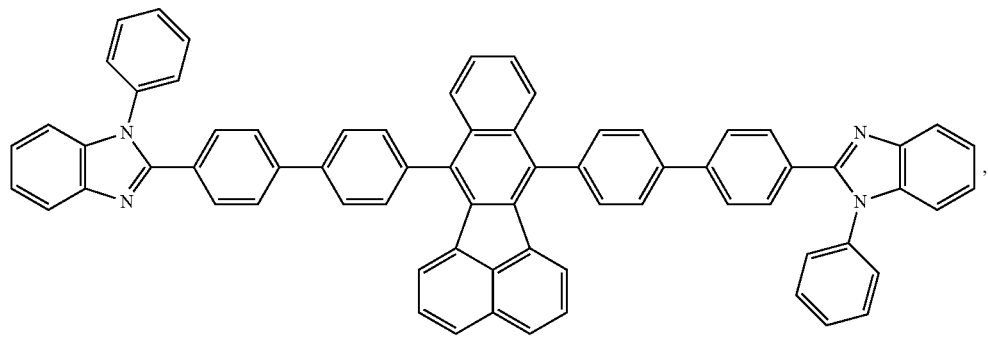
(Formula 9)
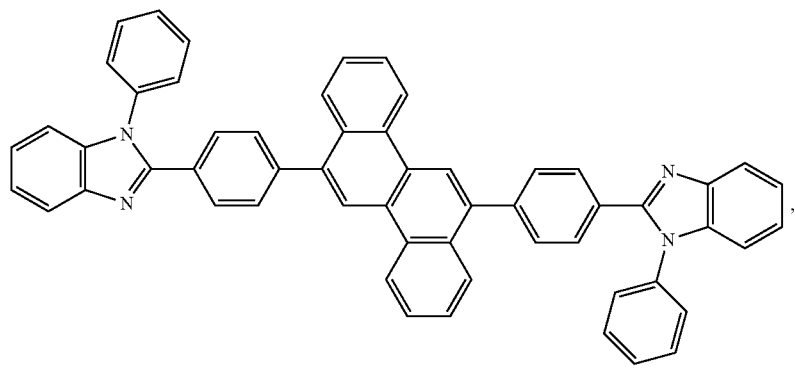
(Formula 17)
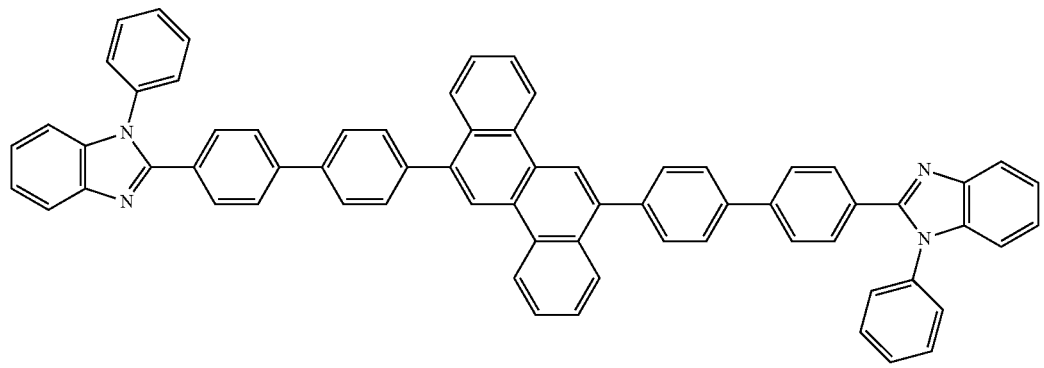

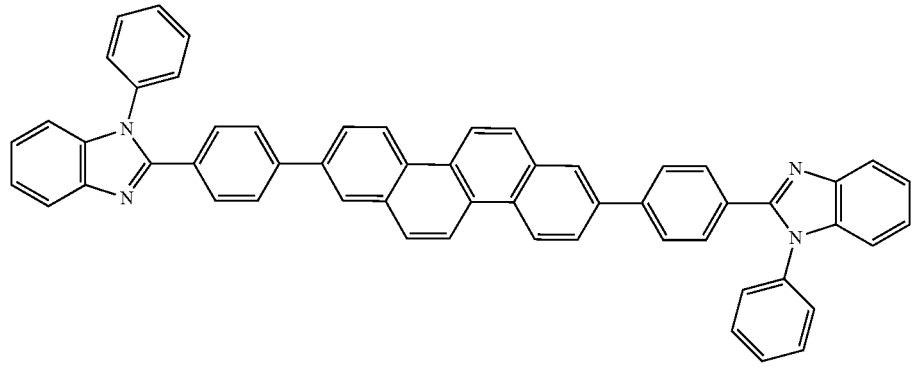

(Formula 23)

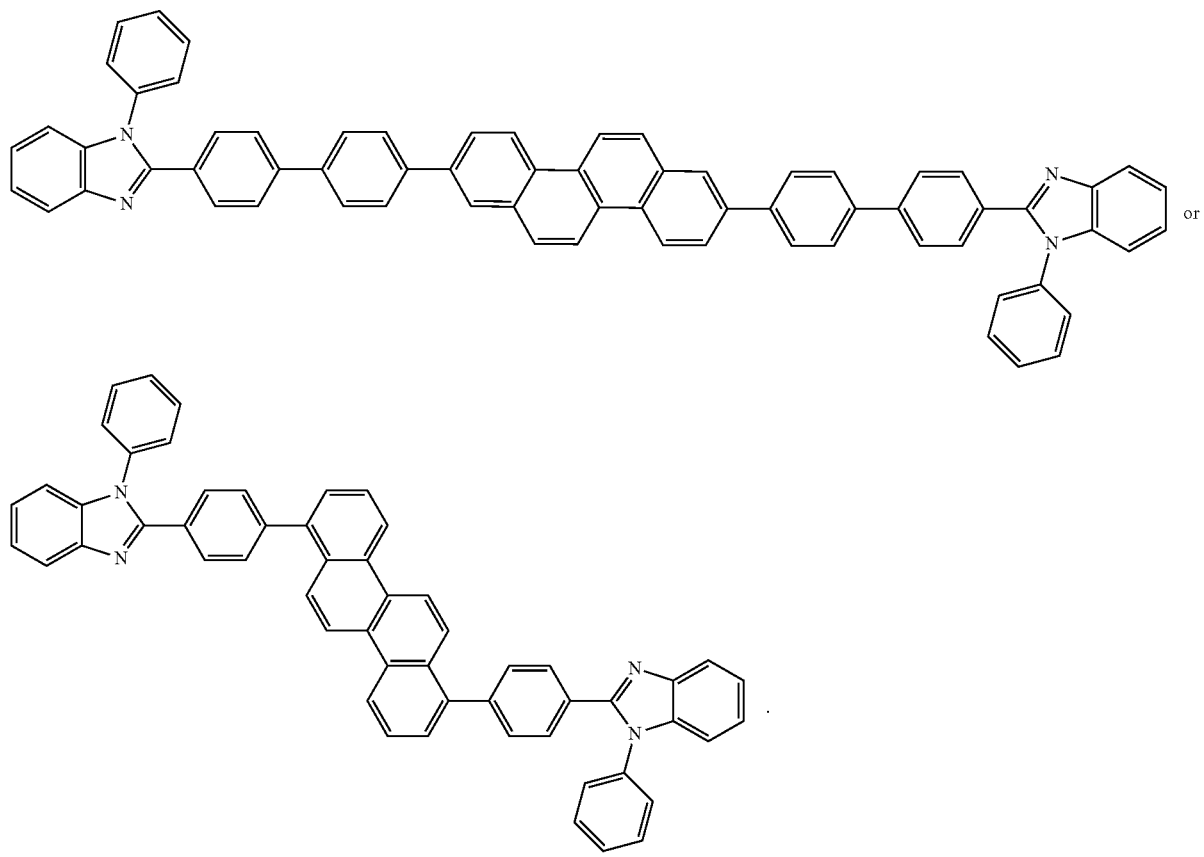

(Formula 24)

or

15. An organic light-emitting diode comprising:
a first electrode;
a second electrode; and
an organic layer between the first electrode and the second electrode, wherein the organic layer comprises an aromatic heterocyclic compound of claim 1.

16. The organic light-emitting diode of claim 15, wherein the organic layer is at least one selected from the group consisting of an emitting layer, an electron transport layer, a hole injection layer, a hole transport layer, and a hole blocking layer.

17. The organic light-emitting diode of claim 15, further comprising at least one selected from the group consisting of a hole injection layer, a hole transport layer, a hole blocking layer, an electron transport layer and an electron injection layer, between the first electrode and the second electrode.

18. A method of manufacturing an organic light-emitting diode, comprising:
forming a first electrode on a substrate;
forming an organic layer comprising an aromatic heterocyclic compound of claim 1 on the first electrode; and
forming a second electrode on the organic layer.

19. The method of claim 18, wherein the organic layer is formed using a method selected from the group consisting of vacuum deposition, spin coating, inkjet printing, screen printing, spray printing, and heat-transfer.

* * * * *